(12) United States Patent
Yun et al.

(10) Patent No.: US 9,145,571 B2
(45) Date of Patent: Sep. 29, 2015

(54) PREPARATION METHOD OF HUMAN METABOLITES OF SIMVASTATIN OR LOVASTATIN USING BACTERIAL CYTOCHROME P450 AND COMPOSITION THEREFOR

(75) Inventors: Chul Ho Yun, Daejeon (KR); Keon Hee Kim, Daejeon (KR); Dong Hyun Kim, Chungcheongnam-Do (KR); Ji Yeon Kang, Daejeon (KR); Sun Ha Park, Gwangju (KR)

(73) Assignee: Chul Ho Yun, Daejeon (KR)

( * ) Notice: Subject to any disclaimer, the term of this patent is extended or adjusted under 35 U.S.C. 154(b) by 241 days.

(21) Appl. No.: 13/391,111

(22) PCT Filed: Aug. 24, 2010

(86) PCT No.: PCT/KR2010/005611
§ 371 (c)(1),
(2), (4) Date: Feb. 17, 2012

(87) PCT Pub. No.: WO2011/025203
PCT Pub. Date: Mar. 3, 2011

(65) Prior Publication Data
US 2012/0202256 A1    Aug. 9, 2012

(30) Foreign Application Priority Data
Aug. 24, 2009 (KR) .......................... 10-2009-0078181

(51) Int. Cl.
*C12P 17/06* (2006.01)
*C12N 9/02* (2006.01)

(52) U.S. Cl.
CPC ............... *C12P 17/06* (2013.01); *C12N 9/0071* (2013.01); *C12Y 114/14001* (2013.01)

(58) Field of Classification Search
None
See application file for complete search history.

(56) References Cited

U.S. PATENT DOCUMENTS

| 2005/0048484 A1* | 3/2005 | Hauer et al. ...................... 435/6 |
| 2005/0059128 A1 | 3/2005 | Arnold et al. |
| 2008/0182303 A1* | 7/2008 | Morgan et al. ................ 435/125 |

OTHER PUBLICATIONS

Boddupalli et al., Fatty acid monooxygenation by P450BM-3: Product identification and proposed mechanisms for the sequential hydroxylation reactions., Archives of Biochemistry and Biophysics (1992), vol. 292, Issue 1, pp. 20-28.*
P14779 (last viewed on Oct. 9, 2013).*
van Vugt-Lussenburg et al., Identification of Critical Residues in Novel Drug Metabolizing Mutants of Cytochrome P450 BM3 Using Random Mutagenesis., J. Med. Chem., Epub Jan. 18, 2007, vol. 50 (3), pp. 455-461.*
WP_025751046.1 (last viewed on Nov. 20, 2014).*
Guo et al., Protein tolerance to random amino acid change, 2004, Proc. Natl. Acad. Sci. USA 101: 9205-9210.*
Lazar et al., Transforming Growth Factor α: Mutation of Aspartic Acid 47 and Leucine 48 Results in Different Biological Activity, 1988, Mol. Cell. Biol. 8:1247-1252.*
Hill et al., Functional Analysis of conserved Histidines in ADP-Glucose Pyrophosphorylase from *Escherichia coli*, 1998, Biochem. Biophys. Res. Comm. 244:573-577.*

(Continued)

*Primary Examiner* — Alexander Kim
(74) *Attorney, Agent, or Firm* — Lathrop & Gage LLP

(57) ABSTRACT

A method of producing human metabolites of simvastatin or lovastatin, and more particularly, a method of producing human metabolites of simvastatin and lovastatin by using bacterial cytochrome P450 BM3(CYP102A1) or mutants thereof, and a composition and kit therefor.

13 Claims, 13 Drawing Sheets

(56) References Cited

OTHER PUBLICATIONS

Wacey et al., Disentangling the perturbational effects of amino acid substitutions in the DNA-binding domain of p53., Hum Genet, 1999, vol. 104, pp. 15-22.*
Bernhardt, R. (2006) "Cytochromes P450 as Versatile Biocatalysts," J Biotechnol 124:128-145.
Capdevila et al. (2002) "Biochemical and Molecular Properties of the Cytochrome P450 Arachidonic Acid Monooxygenases," Prostaglandins & Other Lipid Mediators 68-69:325-344.
Caron et al. (2007) "Predicting the Oxidative Metabolism of Statins: An Application of the MetaSite® Algorithm," Pharm Res. 24(3):480-501.
Di Nardo et al. (2007) "Wild-Type CYP102A1 as a Biocatalyst: Turnover of Drugs Usually Metabolised by Human Liver Enzymes," J Biol Inorg Chem 12:313-323.
Garcia et al. (2003) "Clinical Pharmacokinetics of Statins," Methods Find Exp Clin Pharmacol. 25(6):457-481.
Guengerich et al. (1996) "New Applications of Bacterial Systems to Problems in Toxicology," Crit Rev Toxicol 26(5):551-583.
Guengerich, F.P. (2002) "Cytochrome P450 Enzymes in the Generation of Commercial Products," Nat Rev Drug Discov 1:359-366.
Isin et al. (2006) "Kinetics and Thermodynamics of Ligand Binding by Cytochrome P450 3A4," J Biol Chem 281(14):9127-9136.
Johnson et al. (2004) "Pharmacological Characterization of 4-hydroxy-N-desmethyl Tamoxifen, a Novel Active Metabolite of Tamoxifen," Breast Cancer Res Treat 85:151-159.
Kim et al. (2008) "Heterologous Expression and Characterization of Wild-Type Human Cytochrome P450 1A2 Without Conventional N-Terminal Modification in Escherichia coli," Protein Expr Purif 57:188-200.
Kim et al. (2008) "Generation of Human Metabolites of 7-Ethoxycoumarin by Bacterial Cytochrome P450 BM3," Drug Metab Dispos 36:2166-2170.
Kim et al. (2009) "Generation of the Human Metabolite Piceatannol from the Anti-Cancer Preventive Agent Resveratrol by Bacterial Cytochrome P450 BM3," Drug Metab Dispos 37(5):932-936.
Kitazume et al. (2007) "Obligatory Intermolecular Electron-Transfer from FAD to FMN in Dimeric P450BM-3," Biochemistry 46:11892-11901.
Omura et al. (1964) "The Carbon Monoxide-Binding Pigment of Liver Microsomes, II. Solubilization, Purification, and Properties," J Biol Chem 239(7):2379-2385.
Park et al. (2010) "Engineering Bacterial Cytochrome P450 (P450) BM3 into a Prototype with Human P450 Enzyme Activity Using Indigo Formation," Drug Metab Dispos 38(5):732-739.
Prueksaritanont et al. (1997) "In Vitro Metabolism of Simvastatin in Humans (SBT)Identification of Metabolizing Enzymes and Effect of the Drug on Hepatic P450S," Drug Metabolism and Disposition 25(10):1191-1199.
Prueksaritanont et al. (2002) "Glucuronidation of Statins in Animals and Humans: a Novel Mechanism of Statin Lactonization," Drug Metab Dispos. 30(5):505-12.
Ruettinger et al. (1989) "Coding Nucleotide, 5' Regulatory, and Deduced Amino Acid Sequences of P-450BM-3, a Single Peptide Cytochrome P-450:NADPH-P-450 Reductase from Bacillus megaterium," J. Biol. Chem. 264(19):10987-10995.
Rushmore et al. (2000) "Bioreactor Systems in Drug Metabolism: Synthesis of Cytochrome P450-Generated Metabolites," Metab Eng 2:115-125.
Sawayama et al. (2009) "A Panel of Cytochrome P450 BM3 Variants to Produce Drug Metabolites and Diversify Lead Compounds," Chemistry 15(43):11723-11729.
Transon et al. (1996) "In vitro Comparative Inhibition Profiles of Major Human Drug Metabolising Cytochrome P450 Isozymes (CYP2C9, CYP2D6 and CYP3A4) by HMG-CoA Reductase Inhibitors," Eur J Clin Pharmacol. 50(3):209-215.
Tornio et al. (2005) "Comparison of 3-Hydroxy-3-Methylglutaryl Coenzyme A (HMG-CoA) Reductase Inhibitors (Statins) as Inhibitors of Cytochrome P450 2C8," Basic Clin Pharmacol Toxicol. 97(2):104-10.
Ueng et al. (1997) "Cooperativity in Oxidations Catalyzed by Cytochrome P450 3A4," Biochemistry 36:370-381.
Urlacher et al. (2006) "Cytochrome P450 Monooxygenases: Perspectives for Synthetic Application," Trends Biotechnol 24(7):324-330.
Vail et al. (2005) "Preparative Synthesis of Drug Metabolites Using Human Cytochrome P450s 3A4, 2C9 and 1A2 with NADPH-P450 Reductase Expressed in Escherichia coli," J Ind Microbiol Biotechnol 32:67-74.
Van Vugt-Lussenburg et al. (2006) "Heterotropic and Homotropic Cooperativity by a Drug-Metabolising Mutant of Cytochrome P450 BM3," Biochemical and Biophysical Research Communications 346(3):810-818.
Van Vugt-Lussenburg et al. (2007) "Identification of Critical Residues in Novel Drug Metabolizing Mutants of Cytochrome P450 BM3 Using Random Mutagenesis," J Med Chem 50:455-461.
Vickers et al. (1990) "Metabolic Disposition Studies on Simvastatin, a Cholesterol-Lowering Prodrug," Drug Metab Dispos 18(2):138-145.
Vickers et al. (1990) "In Vitro and In Vivo Biotransformation of Simvastatin, an Inhibitor of HMG CoA Reductase," Drug Metab Dispos. 18(4):476-483.
Vyas et al. (1990) "Biotransformation of Lovastatin, I. Structure Elucidation of In Vitro and In Vivo Metabolites in the Rat and Mouse," Drug Metab Dispos. 18(2):203-211.
Whitehouse et al. (2008) "Evolved CYP102A1 ($P450_{BM3}$) Variants Oxidise a Range of Non-Natural Substrates and Offer New Selectivity Options," Chem Commun pp. 966-968, published online Jan. 11, 2008.
Yun et al. (2006) "Functional Expression of Human Cytochrome P450 Enzymes in Escherichia coli," Curr Drug Metab 7:411-429.
Yun et al. (2007) "The Bacterial P450 BM3: a Prototype for a Biocatalyst with Human P450 Activities," Trends Biotechnol 25(7):289-298.
Notice of Allowance dated Sep. 9, 2012, from the Korean Intellectual Property Office for Korean Patent Application No. 10-2009-0078181 (English translation).
Prueksaritanont et al. (2003), "The human heptic metabolism of simvastatin hydroxyl acid is mediated primarily by CYP3A, and not CYP2D6," Br J Clin Pharmacol. 56(1):120-124.

* cited by examiner

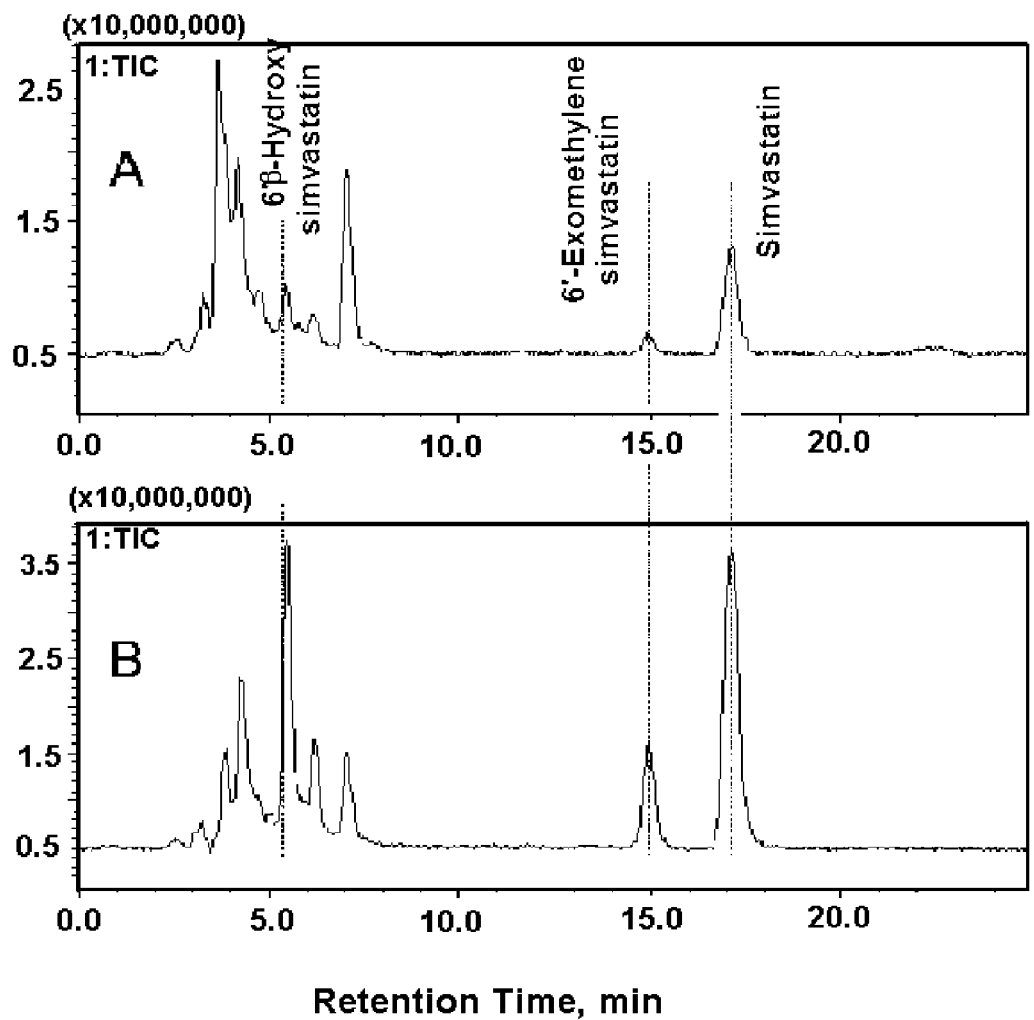

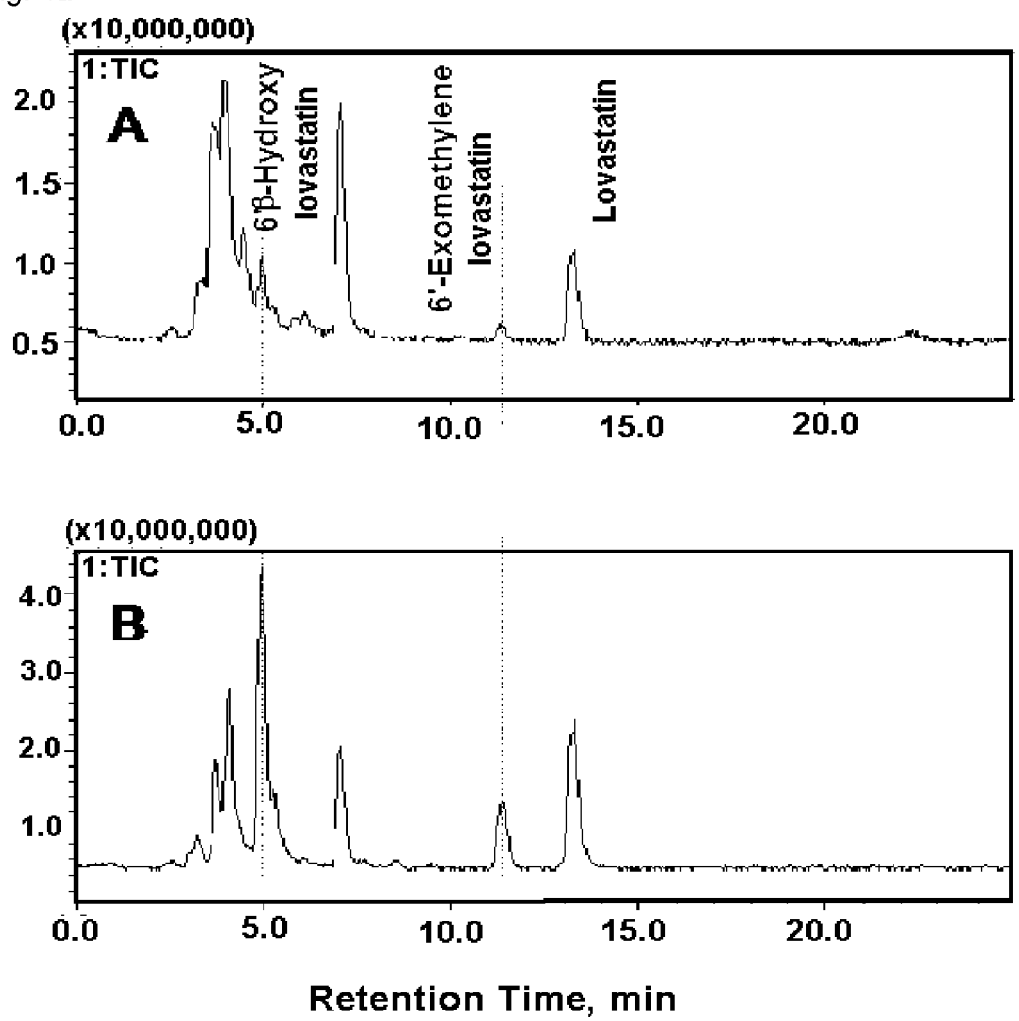

PREPARATION METHOD OF HUMAN METABOLITES OF SIMVASTATIN OR LOVASTATIN USING BACTERIAL CYTOCHROME P450 AND COMPOSITION THEREFOR

CROSS-REFERENCE TO RELATED APPLICATIONS

This application is the U.S. National Stage Application filed under 35 U.S.C. §371 of International Application No. PCT/KR2010/005611, filed on Aug. 24, 2010 and published in English on Mar. 3, 2011 as WO 2011/025203, which claims the benefit of Korean Application No. KR 10-2009-0078181, filed Aug. 24, 2009; all of which are hereby incorporated by reference in their entirety to the extent not inconsistent with the disclosure herein.

TECHNICAL FIELD

The present invention relates to a method of producing human metabolites of simvastatin and lovastatin by using bacterial cytochrome P450 BM3 (CYP102A1) or mutants thereof.

This work was supported in part by the 21C Frontier Microbial Genomics and Application Center Program of the Ministry of Education, Science & Technology of the Republic of Korea and the National Research Foundation of Korea.

1. The 21C Frontier Microbial Genomics and Application Center Program of the Ministry of Education [Project No.: MG08-0306-2-0, Title: Development of humanized bacterial monooxygenase for fine chemicals using microbial cytochrome P450 enzyme genomics]

2. The National Research Foundation of Korea (previously named, Korea Science and Engineering Foundation) [Project No.: R01-2008-000-21072-02008, Title: Development of drug lead compounds using molecular evolution techniques of CYPome]

BACKGROUND ART

Simvastatin and lovastatin are well known anti-hyperlipidemic or anti-hypercholesterolemic drugs and cholesterol lowering agent. Simvastatin is metabolized to at least four primary metabolites, namely 6'β-OH simvastatin, 6'-exomethylene simvastatin, 6'-hydroxymethyl metabolite, and 3'-OH simvastatin. Although CYP3A4 is the main enzyme involved in the primary metabolism of simvastatin, CYPs 2C8 (Tornio et al., 2005), 2C9 (Transon et al., 1996), and 2D6 (Transon et al., 1996) are also involved in the formation of simvastatin metabolites.

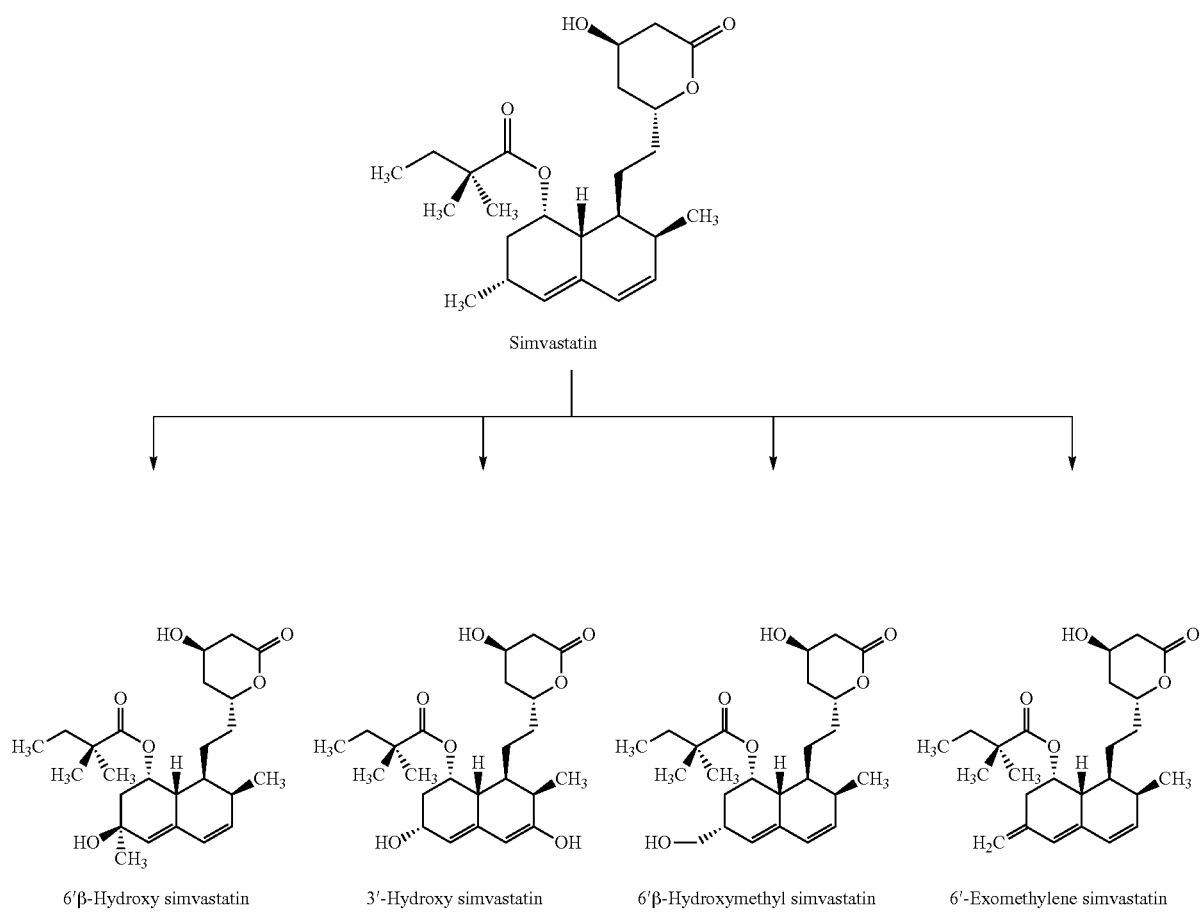

The extensive oxidative metabolism of lovastatin in the human liver is primarily mediated by CYP3A enzymes, particularly CYP3A4, to generate three known metabolites, namely 6'β-OH lovastatin, 3"-OH lovastatin, and 6'-exomethylene metabolites (Garcia et al., 2003; Caron et al., 2007).

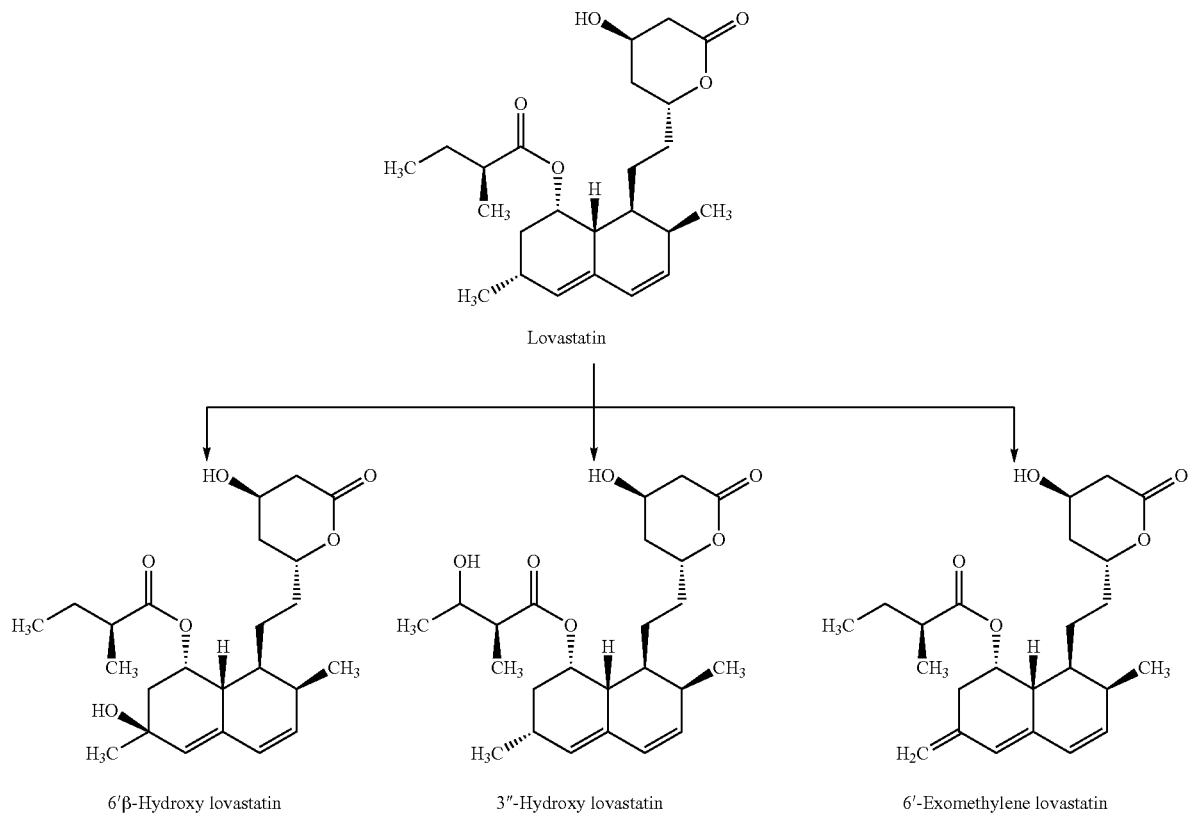 [SMILES: CC[C@H](C)C(=O)O[C@H]1C[C@@H](C)C=C2C=C[C@H](C)[C@H](CC[C@@H]3C[C@@H](O)CC(=O)O3)[C@H]21 ; CC[C@H](C)C(=O)O[C@H]1C[C@](C)(O)C=C2C=C[C@H](C)[C@H](CC[C@@H]3C[C@@H](O)CC(=O)O3)[C@H]21 ; CC(O)[C@H](C)C(=O)O[C@H]1C[C@@H](C)C=C2C=C[C@H](C)[C@H](CC[C@@H]3C[C@@H](O)CC(=O)O3)[C@H]21 ; C=C1C=C2C=C[C@H](C)[C@H](CC[C@@H]3C[C@@H](O)CC(=O)O3)[C@H]2[C@@H](OC(=O)[C@@H](C)CC)C1]

6'β-Hydroxy lovastatin     3"-Hydroxy lovastatin     6'-Exomethylene lovastatin

After oral ingestion, simvastatin and lovastatin, which are inactive lactones, are hydrolyzed to the corresponding mvastatin and lova (Vickers et al., 1990a). This is a principal metabolite and an inhibitor of 3-hydroxy-3-methylglutaryl-coenzyme A (HMG-CoA) reductase. This enzyme catalyzes the conversion of HMG-CoA to mevalonate, which is an early rate limiting step in the biosynthesis of cholesterol. In addition to the P450-mediated oxidation and β-oxidation processes, glucuronidation constitutes a common metabolic pathway for statins (Prueksaritanont et al., 2002). It was found that the metabolites resulting from microsomal oxidation of simvastatin (Vickers et al., 1990) and lovastatin (Vyas et al., 1990) by P450 enzymes are effective inhibitors of the HMG-CoA) reductase. Therefore, it was suggested that the metabolites may contribute to the cholesterol lowering effect of simvastatin and lovastatin. However, systematic studies of safety, efficacy, and toxicity of the metabolites have not yet been carried out. The major metabolites including 6'β-OH statins, have not been prepared by chemical synthesis previously.

Cytochrome P450 enzymes (P450s or CYPs) constitute a large family of enzymes that are remarkably diverse oxygenation catalysts found throughout nature, from archaea, bacteria, fungi, plants, animals and humans http:drnelson<dot>utmen<dot>edu/CytochromeP450<dot>html). Due to their catalytic diversity and broad substrate range, P450s are attractive as biocatalysts in the production of fine chemicals, including pharmaceuticals (Guengerich 2002; Urlacher et al., 2006; Yun et al., 2007; Lamb et al., 2007). In spite of the potential use of mammalian P450s in various biotechnology fields, they are not suitable as biocatalysts mainly because of their low stability and low catalytic activity.

If prodrugs are converted to biologically 'active metabolites' by human liver P450s during the drug development process (Johnson et al., 2004), the pure metabolites are required to understand the drug's efficacy, toxic effect, and pharmacokinetics. When the pure metabolites are difficult to synthesize by chemical methods, using the P450s is a useful alternative to generate the metabolites of drugs or drug candidates. Metabolite preparation has been demonstrated using human liver P450s expressed in *Escherichia coli* (Yun et al., 2006) and in insect cells (Rushmore et al., 2000; Vail et al., 2005), but these systems are still costly and have low productivities due to limited stabilities and slow reaction rates (Guengerich et al., 1996). It was shown that engineering bacterial P450 BM3 could produce human drug metabolites (Yun et al., 2007 and references therein; Kim 2009; Kim 2010; Park 2010). Recently, the Food and Drug Administration (FDA) modified its standards for evaluating drug toxicity, particularly with regard to the toxicity of drug metabolites. In February 2008, the FDA issued the Guidance for Industry: Safety Testing of Drug Metabolites (Food and Drug Administration, Guidance for Industry: Safety Testing of Drug Metabolites; www<dot>fda<dot>gov/downloads/Drugs/Guidance ComplianceRegulatoryInformation/Guidances/ucm079266<dot>pdf). According to this guide, any human drug metabolites " . . . formed at greater than 10 percent of parent drug systemic exposure at steady state should be subject to separate safety testing, that is, by synthesis and administration to test animals (Guengerich, 2009 and references therein). The issue of human metabolites in safety testing (MIST) has presented a challenge at the early stages of drug development for the pharmaceutical industry. Some metabolites of concern can be prepared by chemical methods, but the others may not be easily prepared by the chemical methods. In the later cases, human liver microsomes, heterologously expressed human enzymes in bacteria, and purified human enzymes might be good candidates for biocatalysts to prepare human drug metabolites. However, they have several weaknesses such as low catalytic activity and low stability for industrial use to prepare the metabolites.

All the cited references are incorporated herein by reference in their entireties. The information disclosed herein is intended to assist understanding of the technical background of the present invention, and cannot be prior art.

DISCLOSURE OF INVENTION

Technical Problem

The purpose of the present invention is to provide a method of producing human metabolites of simvastatin and lovastatin which cannot be produced by chemical synthesis on a mass scale, and more particularly, a method of producing human metabolites of simvastatin and lovastatin using an enzyme that stably and efficiently catalyzes a reaction thereof.

Solution to Problem

The present invention provides a method of producing human metabolites of simvastatin and lovastatin using bacterial cytochrome P450 BM3 (CYP102A1) or mutants thereof, and a composition and a kit therefor. The present invention also provides novel mutants of CYP102A1 and an isolated nucleic acid encoding the mutants.

The mutants or composition provided by the present invention can be used to produce human metabolites of simvastatin and lovastatin efficiently. While simvastatin and lovastatin are known to produce at least four and three metabolites, respectively, CYP102A1 mutants produced only two metabolites, one major (6'β-OH statin) and one minor (6'-exomethylene statin) metabolites. Thus the use of wild-type and mutant CYP102A1 is beneficial in the selective production of 6'β-OH statin and 6'-exomethylene statin.

BRIEF DESCRIPTION OF DRAWINGS

The above and other features and advantages of the present invention will become more apparent by describing in detail exemplary embodiments thereof with reference to the attached drawings in which:

FIG. 3a to FIG. 3c show LC-MS elution profiles of simvastatin and its metabolites produced by CYP102A1 mutant #17 and human CYP3A4.

FIG. 4a to FIG. 4c show LC-MS elution profiles of lovastatin and its metabolites produced by CYP102A1 mutant #17 and human CYP3A4.

DETAILED DESCRIPTION OF THE INVENTION

Hereinafter, the present invention will now be described more fully with reference to the accompanying drawings, in which exemplary embodiments of the invention is shown.

The present inventors have found that simvastatin or lovastatin is converted into human metabolites when wild-type CYP102A1 (Seq ID No.16, GenBank Accession Nos. J04832, P14779) and site-directed mutants thereof, which are expressed in *E. coli* (Tables 1 and 2), are incubated with simvastatin or lovastatin in the presence of a NADPH-generating system based on results from high-performance liquid chromatography (HPLC) chromatograms (FIGS. 1 and 2), LC-MS elution profiles (FIGS. 3 and 4), absorption spectra (FIGS. 5 and 6), and nuclear magnetic resonance (NMR) spectroscopy (Tables 3 to 7). While human CYP1A2 oxidizes simvastatin and lovastatin to produce four and three major metabolites, respectively, wild-type CYP102A1 and mutants thereof selectively produce one major 6'β-OH product and one minor 6'-exomethylene product.

A turnover number of 17 types of mutants for the oxidation of statins (production of metabolites) varied over a wide range (Table 8). Mutants #16 and 17 showed higher catalytic activity than human CYP3A4. The turnover number of mutant #17 (10 min$^{-1}$) was 3.3 times and 2040 times higher than those of human CYP3A4 and wild-type CYP102A1, respectively.

Figure 7:
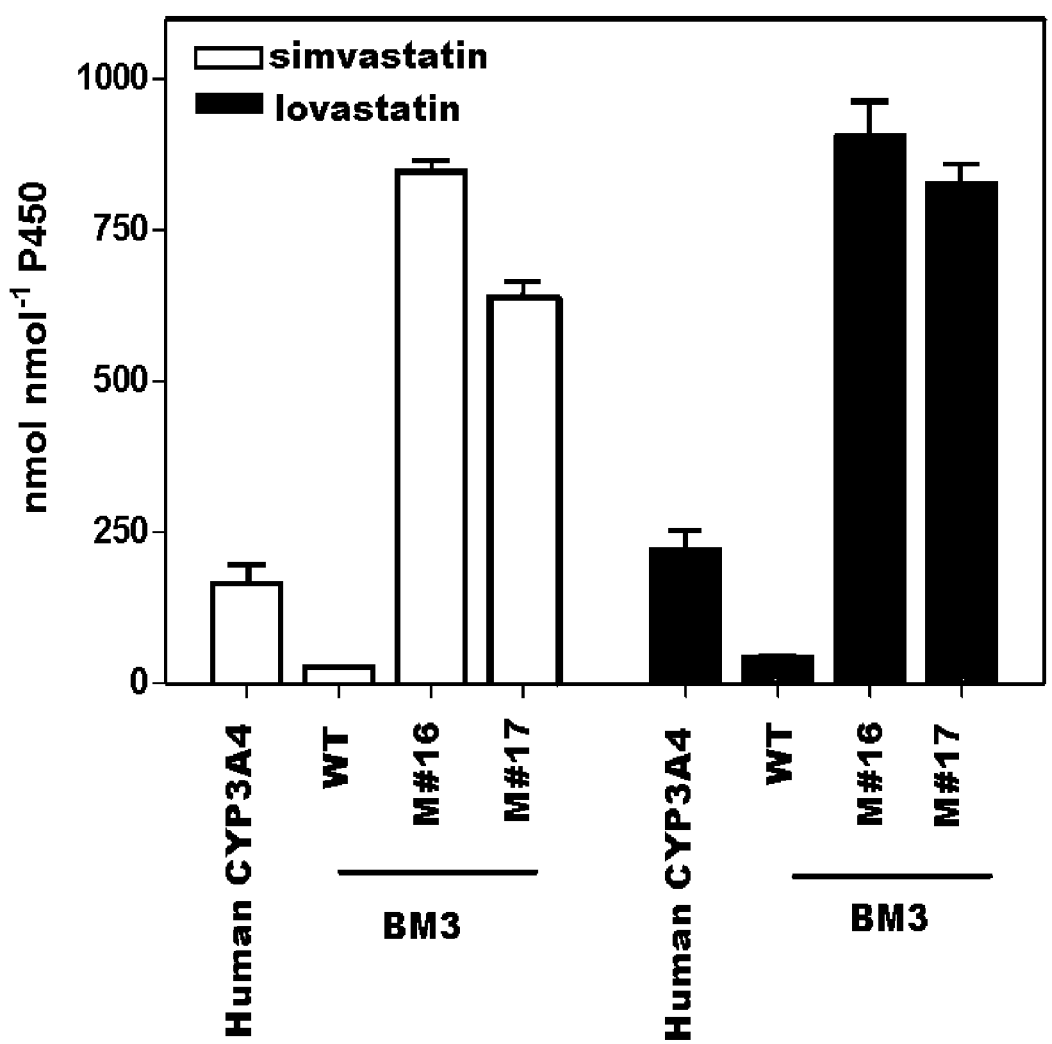
FIG. 7 shows total turnover numbers of 6'β-OH product formation by CYP102A1 mutants.

A total turnover number of mutant #16 was the highest and 5 to 6 times higher than that of human CYP3A4 after a 4 hour reaction and that of wild-type CYP102A1 was 0.77 and 1.9 nmol product/nmol P450 for simvastatin and lovastatin, respectively (Table 9 and FIG.7). Mutants #16 and 17 showed a significantly increased $K_{cat}$ value of 10 min$^{-1}$ for 6'β-hydroxylation reaction of simvastatin and lovastatin. The overall range of $K_m$ values of the CYP102A1 mutants was 37 to 44 μM. Catalytic efficiencies ($K_{cat}/K_m$) of mutant #17 for 6'β-hydroxylation reaction of simvastatin and lovastatin were 0.36 and 0.46 min$^{-1}$ μM$^{-1}$, respectively, which are 7 times or higher than that of human CYP3A4 (Table 10 and FIG. 8).

By using a systematic screening strategy, the inventors found new natural variants of CYP102A1 among CYP102A1s from 16 different strains of *B. megaterium* (Table 11). Among the total 55 substituted amino acid residues of the natural variants relative to that of CYP102A1.1, substitutions of amino acids in reductase domains (residues 473-1048) occurred at a much higher frequency than in heme domain (residues 1-472) (Tables 12 and 13). Further, the inventors prepared various chimeric proteins by exchanging the heme domain of natural variants with that of said CYP102A1 mutants and found that some chimeric proteins showed dramatically higher oxidation activity towards typical human P450 substrates, including lovastatin and simvastatin, than those of mutants in Table 2(Table 14).

Based on these experimental results, the present invention provides novel mutants of CYP102A1 and a composition for catalyzing the reaction of preparing human metabolites of simvastatin or lovastatin, the composition including wild-type CYP102A1 and/or mutant(s) of CYP102A1.

The amino acid seauece of the wild-type CYP102A1 is as follows:

```
                                              (Seq ID No. 16)
TIKEMPQPKT  FGELKNLPLL  NTDKPVQALM  KIADELGEIF

KFEAPGRVTR  YLSSQRLIKE  ACDESRFDKN  LSQALKFVRD

FAGDGLFTSW  THEKNWKKAH  NILLPSFSQQ  AMKGYHAMMV

DIAVQLVQKW  ERLNADEHIE  VPEDMTRLTL  DTIGLCGFNY

RFNSFYRDQP  HPFITSMVRA  LDEAMNKLQR  ANPDDPAYDE

NKRQFQEDIK  VMNDLVDKII  ADRKASGEQS  DDLLTHMLNG

KDPETGEPLD  DENIRYQIIT  FLIAGHETTS  GLLSFALYFL

VKNPHVLQKA  AEEAARVLVD  PVPSYKQVKQ  LKYVGMVLNE

ALRLWPTAPA  FSLYAKEDTV  LGGEYPLEKG  DELMVLIPQL

HRDKTIWGDD  VEEFRPERFE  NPSAIPQHAF  KPFGNGQRAC

IGQQFALHEA  TLVLGMMLKH  FDFEDHTNYE  LDIKETLTLK

PEGFVVKAKS  KKIPLGGIPS  PSTEQSAKKV  RKKAENAHNT

PLLVLYGSNM  GTAEGTARDL  ADIAMSKGFA  PQVATLDSHA

GNLPREGAVL  IVTASYNGHP  PDNAKQFVDW  LDQASADEVK

GVRYSVFGCG  DKNWATTYQK  VPAFIDETLA  AKGAENIADR

GEADASDDFE  GTYEEWREHM  WSDVAAYFNL  DIENSEDNKS

TLSLQFVDSA  ADMPLAKMHG  AFSTNVVASK  ELQQPGSARS

TRHLEIELPK  EASYQEGDHL  GVIPRNYEGI  VNRVTARFGL

DASQQIRLEA  EEEKLAHLPL  AKTVSVEELL  QYVELQDPVT

RTQLRAMAAK  TVCPPHKVEL  EALLEKQAYK  EQVLAKRLTM

LELLEKYPAC  EMKFSEFIAL  LPSIRPRYYS  ISSSPRVDEK

QASITVSVVS  GEAWSGYGEY  KGIASNYLAE  LQEGDTITCF

ISTPQSEFTL  PKDPETPLIM  VGPGTGVAPF  RGFVQARKQL

KEQGQSLGEA  HLYFGCRSPH  EDYLYQEELE  NAQSEGIITL

HTAFSRMPNQ  PKTYVQHVME  QDGKKLIELL  DQGAHFYICG

DGSQMAPAVE  ATLMKSYADV  HQVSEADARL  WLQQLEEKGR

YAKDVWAG
```

The present invention also provides a method of producing human metabolites of simvastatin or lovastatin, the method including reacting at least one enzyme selected from the group consisting of wild-type CYP102A1 and CYP102A1 mutants with simvastatin or lovastatin. The method may further include adding a NADPH-generating system to the reaction.

The present invention also provides a kit for producing human metabolites of simvastatin or lovastatin, the kit including at least one enzyme selected from the group consisting of wild-type CYP102A1 and CYP102A1 mutants and a NADPH-generating system. The kit may further include a reagent required for the progression of reaction.

The NADPH-generating system used for the method of producing human metabolites of simvastatin or lovastatin and the kit may be any system that is known in the art. For example, the NADPH-generating system may include glucose 6-phosphate, NADP+, and yeast glucose 6-phosphate, but is not limited thereto.

The production of human metabolites of simvastatin or lovastatin is conducted at a temperature in the range of 0 to 40° C., and preferably 30 to 40° C.

The CYP102A1 mutants may be prepared using any method that is known in the art, for example, deletion mutation (Kowalski D. et al., J. Biochem., 15, 4457), PCT method, Kunkel method, site-directed mutation, DNA shuffling, staggered extension process (StEP), and error-prone PCR.

The CYP102A1 mutants according to the present invention have an amino acid sequence of the wild-type CYP102A1 modified by natural or artificial substitution, deletion, addition, and/or insertion.

The CYP102A1 mutants according to the present invention include polypeptide having an amino acid sequence which is more than 50% similar, preferably more than 75% similar, and more particularly more than 90%, 95%, 96%, 97%, 98% or 99% similar to the sequence of wild-type CYP102A1.

The amino acid of mutants used or provided by the present invention may be substituted with an amino acid that has similar properties. Preferably, the amino acid of the mutant of CYP102A1 of the present invention may be substituted with an amino acid that has similar properties as classified below. For example, alanine (A), valine (V), leucine (L), isoleucine (I), proline (P), methionine (M), phenylalanine (F), and tryptophan (W) are nonpolar amino acids with similar properties. Glycine (G), serine(s), threonine (T), cysteine (C), tyrosine (Y), asparagine (N), and glutamine (Q) are neutral amino acids, aspartic acid (D) and glutamic acid (E) are acidic amino acids, and lysine (K), arginine (R), and histidine (H) are basic amino acids.

The CYP102A1 mutant of the present invention may include at least one substitution selected from the group consisting of a substitution at a 47th amino acid of the wild-type CYP102A1, i.e., arginine (R), with an amino acid selected from the group consisting of alanine, valine, leucine, isoleucine, proline, methionine, phenylalanine, and tryptophan, a substitution at a 51st amino acid of the wild-type CYP102A1, i.e., tyrosine (Y), with an amino acid selected from the group consisting of alanine, valine, leucine, isoleucine, proline, methionine, phenylalanine, and tryptophan, a substitution at a 64th amino acid of the wild-type CYP102A1, i.e., glutamic acid (E), with an amino acid selected from the group consisting of glycine, serine, threonine, cysteine, tyrosine, asparagine, and glutamine a substitution at a 74th amino acid of the wild-type CYP102A1, i.e., alanine (A), with an amino acid selected from the group consisting of glycine, serine, threonine, cysteine, tyrosine, asparagine, and glutamine, a substitution at a 81st amino acid of the wild-type CYP102A1, i.e., phenylalanine (F), with an amino acid selected from the group consisting of alanine, valine, leucine, isoleucine, proline, methionine, and tryptophan, a substitution at a 86th amino acid of the wild-type CYP102A1, i.e., leucine (L), with an amino acid selected from the group consisting of alanine, valine, isoleucine, proline, methionine, phenylalanine, and tryptophan, a substitution at a 87th amino acid of the wild-type CYP102A1, i.e., phenylalanine (F), with an amino acid selected from the group consisting of alanine, valine, leucine, isoleucine, proline, methionine, and tryptophan, a substitution at a 143rd amino acid of the wild-type CYP102A1, i.e., glutamic acid (E), with an amino acid selected from the group consisting of glycine, serine, threonine, cysteine, tyrosine, asparagine, and glutamine, a substitution at a 188th amino acid of the wild-type CYP102A1, i.e., leucine (L), with an amino acid selected from the group consisting of glycine, serine, threonine, cysteine, tyrosine, asparagine, and glutamine, a substitution at a 264th amino acid of the wild-type CYP102A1, i.e., alanine (A), with an amino acid selected from the group consisting of glycine, serine, threonine, cysteine, tyrosine, asparagine, and glutamine and a substitution at a 267th amino acid of the wild-type CYP102A1, i.e., glutamic acid (E), with an amino acid selected from the group consisting of alanine, valine, leucine, isoleucine, proline, methionine, phenylalanine, and tryptophan.

The said CYP102A1 mutant may include further mutations of a substitution at a 474th amino acid of the wild-type CYP102A1, i.e., alanine (A), with an amino acid selected from the group consisting of valine, leucine, isoleucine, proline, methionine, phenylalanine and tryptophan, a substitution at a 558th amino acid of the wild-type CYP102A1, i.e., glutamic acid (E), with aspartic acid, a substitution at a 664th amino acid of the wild-type CYP102A1, i.e., threonine (T), with an amino acid selected from the group consisting of alanine, valine, leucine, isoleucine, proline, methionine, phenylalanine and tryptophan, a substitution at a 675th amino acid of the wild-type CYP102A1, i.e., proline (P), with an amino acid selected from the group consisting of alanine, valine, leucine, isoleucine, methionine, phenylalanine and tryptophan, a substitution at a 678th amino acid of the wild-type CYP102A1, i.e., alanine (A), with an amino acid selected from the group consisting of glutamic acid and aspartic acid, a substitution at a 687th amino acid of the wild-type CYP102A1, i.e., glutamic acid (E), with an amino acid selected from the group consisting of alanine, valine, leucine, isoleucine, proline, methionine, phenylalanine and tryptophan, a substitution at a 741st amino acid of the wild-type CYP102A1, i.e., alanine (A), with an amino acid selected from the group consisting of glycine, serine, threonine, cysteine, tyrosine, asparagine and glutamine, a substitution at a 813rd amino acid of the wild-type CYP102A1, i.e., lysine (K), with an amino acid selected from the group consisting of glutamic acid and aspartic acid, a substitution at a 825th amino acid of the wild-type CYP102A1, i.e., arginine (R), with an amino acid selected from the group consisting of glycine, serine, threonine, cysteine, tyrosine, asparagine and glutamine, a substitution at a 836th amino acid of the wild-type CYP102A1, i.e., arginine (R), with an amino acid selected from the group consisting of lysine and histidine, a substitution at a 870th amino acid of the wild-type CYP102A1, i.e., glutamic acid (E), with an amino acid selected from the group consisting of glycine, serine, threonine, cysteine, tyrosine, asparagines, and glutamine, a substitution at a 881st amino acid of the wild-type CYP102A1, i.e., isoleucine (I), with an amino acid selected from the group consisting of alanine, valine, leucine, proline, methionine, phenylalanine and tryptophan, a substitution at a 887th amino acid of the wild-type CYP102A1, i.e., glutamic acid (E), with an amino acid selected from the group consisting of glycine, serine, threonine, cysteine, tyrosine, asparagines, and glutamine, a substitution at a 894th amino acid of the wild-type CYP102A1, i.e., proline (P), with an amino acid selected from the group consisting of glycine, serine, threonine, cysteine, tyrosine, asparagine, and glutamine, a substitution at a 954th amino acid of the wild-type CYP102A1, i.e., serine (S), with an amino acid selected from the group consisting of glycine, threonine, cysteine, tyrosine, asparagines, and glutamine, a substitution at a 967th amino acid of the wild-type CYP102A1, i.e., methionine (M), with an amino acid selected from the group consisting of alanine, valine, leucine, isoleucine, proline, phenylalanine and tryptophan, a substitution at a 981st amino acid of the wild-type CYP102A1, i.e., glutamine (Q), with an amino acid selected from the group consisting of lysine, arginine and histidine, a substitution at a 1008th amino acid of the wild-type CYP102A1, i.e., alanine (A), with an amino acid selected from the group consisting of aspartic acid and glutamic acid, a substitution at a 1021st amino acid of the wild-type CYP102A1, i.e., histidine (H), with an amino acid selected from the group consisting of glycine, serine, threonine, cysteine, tyrosine, asparagine and glutamine and a substitution at a 1022nd amino acid of the wild-type CYP102A1, i.e., glutamine (Q), with an amino acid selected from the group consisting of aspartic acid and glutamic acid. Alternatively, the said CYP102A1 mutant may include further mutations of a substitution at a 473rd amino acid of the wild-type CYP102A1, i.e., lysine (K), with an amino acid selected from the group consisting of glycine, serine, threonine, cysteine, tyrosine, asparagine and glutamine, a substitution at a 474th amino acid of the wild-type CYP102A1, i.e., alanine (A), with an amino acid selected from the group consisting of valine, leucine, isoleucine, proline, methionine, phenylalanine and tryptophan, a substitution at a 546th amino acid of the wild-type CYP102A1, i.e., glutamine (Q), with an amino acid selected from the group consisting of glutamic acid and aspartic acid, a substitution at a 599th amino acid of the wild-type CYP102A1, i.e., aspartic acid (D), with glutamic acid, a substitution at a 624th amino acid of the wild-type CYP102A1, i.e., valine (V), with an amino acid selected from the group consisting of alanine, leucine, isoleucine, proline, methionine, phenylalanine and tryptophan, a substitution at a 637th amino acid of the wild-type CYP102A1, i.e., aspartic acid (D), with glutamic acid, a substitution at a 639th amino acid of the wild-type CYP102A1, i.e., lysine (K), with an amino acid selected from the group consisting of alanine, valine, leucine, isoleucine, proline, methionine, phenylalanine and tryptophan, a substitution at a 660th amino acid of the wild-type CYP102A1, i.e., glycine (G), with an amino acid selected from the group consisting of arginine, lysine and histidine, a substitution at a 664th amino acid of the wild-type CYP102A1, i.e., threonine (T), with an amino acid selected from the group consisting of alanine, valine, leucine, isoleucine, proline, methionine, phenylalanine and tryptophan, a substitution at a 674th amino acid of the wild-type CYP102A1, i.e., glutamine (Q), with an amino acid selected from the group consisting of arginine, lysine and histidine, a substitution at a 715th amino acid of the wild-type CYP102A1, i.e., threonine (T), with an amino acid selected from the group consisting of alanine, valine, leucine, isoleucine, proline, methionine, phenylalanine and tryptophan, a substitution at a 716th amino acid of the wild-type CYP102A1, i.e., alanine (A), with an amino acid selected from the group consisting of glycine, serine, threonine, cysteine, tyrosine, asparagine and glutamine, a substitution at a 741st amino acid of the wild-type CYP102A1, i.e., alanine (A), with an amino acid selected from the group consisting of glycine, serine, threonine, cysteine, tyrosine, asparagine and glutamine, a substitution at a 782nd amino acid of the wild-type CYP102A1, i.e., alanine (A), with an amino acid selected from the group consisting of valine, leucine, isoleucine, proline, methionine, phenylalanine and tryptophan, a substitution at a 813rd amino acid of the wild-type CYP102A1, i.e., lysine (K), with an amino acid selected from the group consisting of glutamic acid and aspartic acid, a substitution at a 824th amino acid of the wild-type CYP102A1, i.e., isoleucine (I), with an amino acid selected from the group consisting of alanien, valine, leucine, proline, methionine, phenylalanine and tryptophan, a substitution at a 870th amino acid of the wild-type CYP102A1, i.e., glutamic acid (E), with an amino acid selected from the group consisting of glycine, serine, threonine, cysteine, tyrosine, asparagine and glutamine, a substitution at a 881st amino acid of the wild-type CYP102A1, i.e., isoleucine (I), with an amino acid selected from the group consisting of alanine, valine, leucine, proline, methionine, phenylalanine and tryptophan, a substitution at a 887th amino acid of the wild-type CYP102A1, i.e., glutamic acid (E), with an amino acid selected from the group consisting of glycine, serine, threonine, cysteine, tyrosine, asparagine and glutamine, a substitution at a 893rd amino acid of the wild-type CYP102A1, i.e., aspartic acid (D), with an amino acid selected from the group consisting of glycine, serine, threonine, cysteine, tyrosine, asparagine and glutamine, a substitution at a 947th amino acid of the wild-type CYP102A1, i.e., glutamic acid (E), with an amino acid selected from the group consisting of lysine, arginine and histidine, a substitution at a 954th amino acid of the wild-type CYP102A1, i.e., serine (S), with an amino acid selected from the group consisting of glycine, threonine, cysteine, tyrosine, asparagine and glutamine, a substitution at a 967th amino acid of the wild-type CYP102A1, i.e., methionine (M), with an amino acid selected from the group consisting of alanine, valine, leucine, isoleucine, proline, phenylalanine and tryptophan, a substitution at a 1008th amino acid of the wild-type CYP102A1, i.e., alanine (A), with an amino acid selected from the group consisting of aspartic acid and glutamic acid and a substitution at a 1019th amino acid of the wild-type CYP102A1, i.e., aspartic acid (D), with glutamic acid.

Preferably, the CYP102A1 mutant of the present invention may include at least one substitution selected from the group consisting of a substitution at a 47th amino acid of the wild-type CYP102A1, i.e., arginine (R), with leucine (L), a substitution at a 51st amino acid of the wild-type CYP102A1, i.e., tyrosine (Y), with phenylalanine (F), a substitution at a 64th amino acid of the wild-type CYP102A1, i.e., glutamic acid (E), with glycine (G), a substitution at a 74th amino acid of the wild-type CYP102A1, i.e., alanine (A), with glycine (G), a substitution at a 81st amino acid of the wild-type CYP102A1, i.e., phenylalanine (F), with isoleucine (I), a substitution at a 86th amino acid of the wild-type CYP102A1, i.e., leucine (L), with isoleucine (I), a substitution at a 87th amino acid of the wild-type CYP102A1, i.e., phenylalanine (F), with valine (V) or alanine (A), a substitution at a 143rd amino acid of the wild-type CYP102A1, i.e., glutamic acid (E), with glycine (G), a substitution at a 188th amino acid of the wild-type CYP102A1, i.e., leucine (L), with glutamine (Q), and a substitution at a 267th amino acid of the wild-type CYP102A1, i.e., glutamic acid (E), with valine (V).

The said CYP102A1 mutant may include further mutations of a substitution at a 474th amino acid of the wild-type CYP102A1, i.e., alanine (A), with valine (V), a substitution at a 558th amino acid of the wild-type CYP102A1, i.e., glutamic acid (E), with aspartic acid (D), a substitution at a 664th amino acid of the wild-type CYP102A1, i.e., threonine (T), with alanine (A), a substitution at a 675th amino acid of the wild-type CYP102A1, i.e., proline (P), with leucine (L), a substitution at a 678th amino acid of the wild-type CYP102A1, i.e., alanine (A), with glutamic acid (E), a substitution at a 687th amino acid of the wild-type CYP102A1, i.e., glutamic acid (E), with an alanine (A), a substitution at a 741st amino acid of the wild-type CYP102A1, i.e., alanine (A), with glycine (G), a substitution at a 813rd amino acid of the wild-type CYP102A1, i.e., lysine (K), with glutamic acid (E), a substitution at a 825th amino acid of the wild-type CYP102A1, i.e., arginine (R), with serine (S), a substitution at a 836th amino acid of the wild-type CYP102A1, i.e., arginine (R), with histidine (H), a substitution at a 870th amino acid of the wild-type CYP102A1, i.e., glutamic acid (E), with asparagine (N), a substitution at a 881st amino acid of the wild-type CYP102A1, i.e., isoleucine (I), with valine (V), a substitution at a 887th amino acid of the wild-type CYP102A1, i.e., glutamic acid (E), with glycine (G), a substitution at a 894th amino acid of the wild-type CYP102A1, i.e., proline (P), with serine (S), a substitution at a 954th amino acid of the wild-type CYP102A1, i.e., serine (S), with asparagine (N), a substitution at a 967th amino acid of the wild-type CYP102A1, i.e., methionine (M), with valine (V), a substitution at a 981st amino acid of the wild-type CYP102A1, i.e., glutamine (Q), with arginine (R), a substitution at a 1008th amino acid of the wild-type CYP102A1, i.e., alanine (A), with aspartic acid (D), a substitution at a 1021st amino acid of the wild-type CYP102A1, i.e., histidine (H), with tyrosine (Y), and a substitution at a 1022nd amino acid of the wild-type CYP102A1, i.e., glutamine (Q), with glutamic acid. Alternatively, the said CYP102A1 mutant may include further mutations of a substitution at a 473rd amino acid of the wild-type CYP102A1, i.e., lysine (K), with threonine (T), a substitution at a 474th amino acid of the wild-type CYP102A1, i.e., alanine (A), with valine (V), a substitution at a 546th amino acid of the wild-type CYP102A1, i.e., glutamine (Q), with glutamic acid (E), a substitution at a 599th amino acid of the wild-type CYP102A1, i.e., aspartic acid (D), with glutamic acid (E), a substitution at a 624th amino acid of the wild-type CYP102A1, i.e., valine (V), with leucine (L), a substitution at a 637th amino acid of the wild-type CYP102A1, i.e., aspartic acid (D), with glutamic acid (E), a substitution at a 639th amino acid of the wild-type CYP102A1, i.e., lysine (K), with alanine (A), a substitution at a 660th amino acid of the wild-type CYP102A1, i.e., glycine (G), with arginine (R), a substitution at a 664th amino acid of the wild-type CYP102A1, i.e., threonine (T), with alanine (A), a substitution at a 674th amino acid of the wild-type CYP102A1, i.e., glutamine (Q), with lysine (K), a substitution at a 715th amino acid of the wild-type CYP102A1, i.e., threonine (T), with alanine (A), a substitution at a 716th amino acid of the wild-type CYP102A1, i.e., alanine (A), with threonine (T), a substitution at a 741st amino acid of the wild-type CYP102A1, i.e., alanine (A), with glycine (G), a substitution at a 782nd amino acid of the wild-type CYP102A1, i.e., alanine (A), with valine (V), a substitution at a 813rd amino acid of the wild-type CYP102A1, i.e., lysine (K), with glutamic acid (E), a substitution at a 824th amino acid of the wild-type CYP102A1, i.e., isoleucine (I), with methionine (M), a substitution at a 870th amino acid of the wild-type CYP102A1, i.e., glutamic acid (E), with asparagine (N), a substitution at a 881st amino acid of the wild-type CYP102A1, i.e., isoleucine (I), with valine (V), a substitution at a 887th amino acid of the wild-type CYP102A1, i.e., glutamic acid (E), with glycine (G), a substitution at a 893rd amino acid of the wild-type CYP102A1, i.e., aspartic acid (D), with glycine (G), a substitution at a 947th amino acid of the wild-type CYP102A1, i.e., glutamic acid (E), with lysine (K), a substitution at a 954th amino acid of the wild-type CYP102A1, i.e., serine (S), with asparagine (N), and glutamine, a substitution at a 967th amino acid of the wild-type CYP102A1, i.e., methionine (M), with valine (V), a substitution at a 1008th amino acid of the wild-type CYP102A1, i.e., alanine (A), with aspartic acid (D) and a substitution at a 1019th amino acid of the wild-type CYP102A1, i.e., aspartic acid (D), with glutamic acid (E).

More preferably, the mutants of CYP102A1 of the present invention may comprise substitution mutations selected from the group consisting of F87A, A264G, F87A/A264G, R47L/Y51F, R47L/Y51F/A264G, R47L/Y51F/F87A, R47L/Y51F/F87A/A264G, A74G/F87V/L188Q, R47L/L86I/L188Q, R47L/F87V/L188Q, R47L/F87V/L188Q/E267V, R47L/L86I/L188Q/E267V, R47L/L86I/F87V/L188Q, R47L/F87V/E143G/L188Q/E267V, R47L/E64G/F87V/E143G/L188Q/E267V, R47L/F81I/F87V/E143G/L188Q/E267V, and R47L/E64G/F81I/F87V/E143G/L188Q/E267V. The said CYP102A1 mutant may include further substitutions of A474V/E558D/T664A/P675L/A678E/E687A/A741G/K813E/R825S/R836H/E870N/I 881V/E887G/P894S/S954N/M967V/Q981R/A1008D/H1021Y/Q1022E. Alternatively, the said CYP102A1 mutant may include further mutations of K473T/A474V/Q546E/D599E/V624L/D637E/K639A/G660R/T664A/Q674K/T715A/A716T/A741G/A782V/K813E/I824M/E870N/I881V/E887G/D893G/E947K/S954N/M967V/A1008D/D1019E.

Most preferably, the mutants of CYP102A1 of the present invention may comprise substitution mutations selected from the group consisting of R47L/F81I/F87V/E143G/L188Q/E267V (M#16), R47L/E64G/F81I/F87V/E143G/L188Q/E267V (M#17), R47L/L86I/F87V/L188Q/A474V/E558D/T664A/P675L/A678E/E687A/A741G/K813 E/R825S/R836H/E870N/I881V/E887G/P894S/S954N/M967V/Q981R/A1008D/H1021Y/Q1022E (M#13V2), R47L/E64G/F87V/E143G/L188Q/E267V/A474V/E558D/T664A/P675L/A678E/E687 A/A741G/K813E/R825S/R836H/E870N/I881V/E887G/P894S/S954N/M967V/Q981R/A1008D/H1021Y/Q1022E (M#15V3), R47L/F81I/F87V/E143G/L188Q/E267V/A474V/E558D/T664A/P675L/A678E/E687A/A741G/K813E/R825S/R836H/E870N/I881V/E887G/P894S/S954N/M967V/Q981R/A1008D/H1021Y/Q1022E (M#16V2), R47L/E64G/F81I/F87V/E143G/L188Q/E267V/A474V/E558D/T664A/P675L/A678E/E687A/A741G/K813E/R825S/R836H/E870N/I881V/E887G/P894S/S954N/M967V/Q981R/A1008D/H1021Y/Q1022E (M#17V2), and R47L/E64G/F81I/F87V/E143G/L188Q/E267V/K473T/A474V/Q546E/D599E/V624L/D637E/K639A/G660R/T664A/Q674K/T715A/A716T/A741G/A782V/K813E/I824M/E870N/I881V/E887G/D893G/E947K/S954N/M967V/A1008D/D1019E (M#17V8).

The present invention also provides isolated nucleic acid molecules encoding novel mutants of CYP102A1 described in this specification.

Protein and nucleic acid according to the present invention may be prepared using various methods known in the art. For example, protein may be prepared by genetic engineering techniques, peptide synthesis using solid-phase techniques (Merrifield, J. Am. Chem. Soc., 85:2149-2154 (1963)), or method of cleaving protein using peptidase. Protein according to the present invention may be natural protein or may be prepared by a recombination of culturing cells transformed with DNA encoding CYP102A1 or mutants thereof and collecting the protein. Protein may be prepared by inserting nucleic acid molecules encoding protein according to the present invention into an expression vector, transforming the vector into a host cell, and purifying protein expressed by the transformed host cell.

For example, the vector may be plasmid, cosmid, a virus, or phage. The host cell into which DNA in the vector is closed or expressed may be a prokaryotic cell, a yeast cell, and a eukaryotic cell. Culture conditions such as a culture medium, temperature, and pH may be selected by those of ordinary skill in the art without undue experiment. In general, principles, protocols, and techniques to maximize productivity of the culture of cells may refer to Mammalian Cell Biotechnology: a Practical Approach, M. Butler, ed. (IRL Press, 1991).

The expression and cloning vector may include a promoter that is operationally linked to a nucleic acid sequence that encodes CYP102A1 or mutants thereof inducing the synthesis of mRNA. A variety of promoters that are recognizable by host cells are known. A promoter suitable for a prokaryotic host cell may be a β-lactamase and lactose promoter system, alkali phosphatase, a tryptophan (trp) promoter system, and a hybrid promoter, for example, a tac promoter. In addition, the promoter used in bacterial systems may include a Shine-Dalgarno (S.D.) sequence operationally linked to DNA that encodes CYP102A1 mutants. A promoter suitable for a yeast host cell may include 3-phosphooglycerate kinase or other glucosidases.

The present invention will be described in further detail with reference to the following examples. These examples are for illustrative purposes only and are not intended to limit the scope of the present invention.

EXAMPLES

Simvastatin and lovastatin were obtained from Merck (Rahway, N.J.). NADPH was purchased from Sigma-Aldrich (St. Louis, Mo., USA). Other chemicals were of the highest grade commercially available.

Example 1

Construction of P450 BM3 Mutants by Site-Directed Mutagenesis

The CYP102A1 mutants used in this study were selected based on earlier work showing their increased catalytic activity toward several human substrates (Kim et al., 2008b and references therein; Park et al., 2010). Each mutant bears the amino acid substitution(s) relative to wild-type CYP102A1, as summarized in Table2.

PCR primers used to introduce BamHI/SacI restriction sites and to induce mutation are listed in Table 1. Codons for amino acid substitution are in italics and are underlined. The PCR primers were obtained from Genotech (Daejeon, Korea). Genes that encode CYP102A1 mutants were amplified from pCWBM3 by PCR primers designed to facilitate cloning into an expression vector pCWori (Dr. F. W. Dahlquist, University of California, SantaBarbara, Calif.) or pSE420 (Invitrogen) (Farinas, et al., 2001). Oligonucleotide assembly was performed by PCR using the primers listed in Table 1. The amplified genes were subsequently cloned into PCWBM3 BamHI/SacI vector at the BamHI/SacI restriction sites. These plasmids were transformed into *Escherichia coli* DH5αF'-IQ (Invitrogen), and this strain was also used to express the mutant CYP102A1 proteins. After mutagenesis, the presence of the desired mutations was confirmed by DNA sequencing (Genotech, Daejeon, Korea)

TABLE 1

[Table 1]

Primers Used to Prepare Mutants

| Name | Sequence |
|---|---|
| BamHI forward | 5'-AGC *GGA TC* C ATG ACA ATT AAA GAA ATG CCT C-3' |
| SacI reverse | 5'-ATC GAG CTC GTA GTT TGT AT-3' |
| R47L | 5'-GCG CCT GGT *CTG* GTA ACG CG -3' |
| Y51F | 5'-GTA ACG CGC *TTC* TTA TCA AGT-3' |
| E64G | 5'-GCA TGC GAT *GGC* TCA CGC TTT-3' |
| A74G | 5'-TAAGT CAA *GGC* CTT AAA TTT GTA CG-3' |
| F81I | 5'-GTA CGT GAT *ATT* GCA GGA GAC-3' |
| L86I | 5'-GGA GAC GGG *ATT* TTT ACA AGC T-3' |
| F87A | 5'-GAC GGG TTA *GCG* ACA AGC TGG-3' |
| F87V | 5'-GAC GGG TTA *GTG* ACA AGC TGG-3' |
| E143G | 5'-GAA GTA CCG *GGC* GAC ATG ACA-3' |
| L188Q | 5'-ATG AAC AAG *CAG* CAG CGA GCA A-3' |
| A264G | 5'-TTC TTA ATT *GGG* GGA CAC GTG-3' |
| E267V | 5'-T GCG GGA CAC *GTG* ACA ACA AGT-3' |
| L86I/F87V | 5'-GGA GAC GGG *ATT GTG* ACA AGC TG-3' |

Example 2

Expression and Purification of Wild-Type CYP102A1 and Mutants Thereof

Wild-type and mutant CYP102A1 were expressed in *Escherichia coli* strain DH5F'-IQ and purified as described in Kim et al., 2008b. A culture was inoculated from a single colony into 5 m of a Luria-Bertani medium supplemented with ampicillin (100 μg/ml) and grown at 37° C. This culture was inoculated into 250 ml of a Terrific Broth medium supplemented with ampicillin (100 μg/ml). The cells were grown at 37° C. with shaking at 250 rpm to an $OD_{600}$ of up to 0.8, at which gene expression was induced by the addition of isopropyl-β-D-thiogalactopyranoside to a final concentration of 0.5 mM. δ-aminolevulinic acid (0.1 mM) was also added thereto. Following induction, the culture was allowed to grow another 36 hours at 30° C. Cells were harvested by centrifugation (15 min, 5000 g, 4° C.). The cell pellet was resuspended in a TES buffer (100 mM Tris-HCL, pH7.6, 500 mM sucrose, 0.5 mM EDTA) and lysed by sonication (Sonicator; Misonix, Inc., Farmingdale, N.Y.). After the lysates was centrifuged at 100,000 g (90 min, 4° C.), a soluble cytosolic fraction was collected and used for the activity assay. The soluble cytosolic fraction was dialyzed from a 50 mM potassium phosphate buffer (pH 7.4) and stored at −80° C. The cytosolic fraction was used within 1 month of manufacture.

The CYP102A1 concentrations were determined from CO-difference spectra as described by Omura and Sato (1964) using $\epsilon = 91$ mM/cm. For all of the wild-type and mutants, a typical culture yielded 300 to 700 nM P450. The expression level of wild-type and mutant CYP102A1 was typically in the range of 1.0 to 2.0 nmol P450/mg cytosolic protein.

Several mutants with high catalytic activity for some substrates in human were selected, and the substitution sites in the mutants are shown in Table 2.

TABLE 2

| Abbreviations | BM3 Wild type and mutants | Ref |
|---|---|---|
| WT | BM3 Wild type | |
| mutant #1 | F87A | Carmichael et al., 2001 |
| mutant #2 | A264G | Carmichael et al., 2001 |
| mutant #3 | F87A/A264G | Carmichael et al., 2001 |
| mutant #4 | R47L/Y51F | Carmichael et al., 2001 |
| mutant #5 | R47L/Y51F/A264G | Carmichael et al., 2001 |
| mutant #6 | R47L/Y51F/F87A | Carmichael et al., 2001 |
| mutant #7 | R47L/Y51F/F87A/A264G | Carmichael et al., 2001 |
| mutant #8 | A74G/F87V/L188Q | Li et al., 2001 |
| mutant #9 | R47L/L86I/L188Q | Kim et al., 2008a |
| mutant #10 | R47L/F87V/L188Q | van Vugt-Lussenbrg et al., 2007 |
| mutant #11 | R47L/F87V/L188Q/E267V | van Vugt-Lussenbrg et al., 2007 |
| mutant #12 | R47L/L86I/L188Q/E267V | Kim et al., 2008 |
| mutant #13 | R47L/L86I/F87V/L188Q | van Vugt-Lussenbrg et al., 2007 |
| mutant #14 | R47L/F87V/E143G/L188Q/E267V | Kim et al., 2008a |
| mutant #15 | R47L/E64G/F87V/E143G/L188Q/E267V | Kim et al., 2008a |
| mutant #16 | R47L/F81I/F87V/E143G/L188Q/E267V | Kim et al., 2008a |
| mutant #17 | R47L/E64G/F81I/F87V/E143G/L188Q/E267V | van Vugt-Lussenbrg et al., 2007 |

Mutants of CYP102A1 used in the Present Invention

Example 3

Oxidation of Simvastatin and Lovastatin by Wild-Type P450 BM3 and Mutants Thereof It was examined whether CYP102A1 and mutants thereof can oxidize simvastatin and lovastatin. Typical steady-state reactions for the oxidation of simvastatin and lovastatin included 50 pmol CYP102A1 in 0.25 ml of 100 mM potassium phosphate buffer (pH 7.4) along with a specified amount of substrate. To determine the kinetic parameters of several CYP102A1 mutants, 2 to 200 μM of statins were used. An aliquot of a NADPH-generating system was used to initiate reactions (final concentrations: 10 mM glucose 6-phosphate, 0.5 mM NADP+, and 1 IU yeast glucose 6-phosphate per ml). A stock solution of statins (20 mM) was prepared in DMSO and diluted into the enzyme reactions with a final organic solvent concentration of <1% (v/v).

In the case of human CYP3A4 activity assay, a control experiment of 50 pmol P450, 100 pmol NADPH-P450 reductase (CPR), 100 pmol cytocrhome $b_5$, and 45 μM L-α-dilauroyl-sn-glycero-3-phosphocholine (DLPC) was used instead of 50 pmol CYP102A1. After the solution was incubated for 30 minutes at 37° C., the reaction was terminated with 2-fold of ice-cold dichloromethane.

Example 3-1

HPLC Analysis

After centrifugation of the reaction mixture, the supernatant was carefully removed and the solvent was evaporated under $N_2$ gas as described in Vickers et al., 1990. The products were analyzed by HPLC using a Gemini $C_{18}$ column (4.6 mm×150 mm, 5 μm, Phenomenex, Torrance, Calif.) with a mobile phase of acetonitrile/water (70/30, v/v) containing 2.5 mM formic acid. Eluates were detected by UV at 238 nm.

Figure 1:
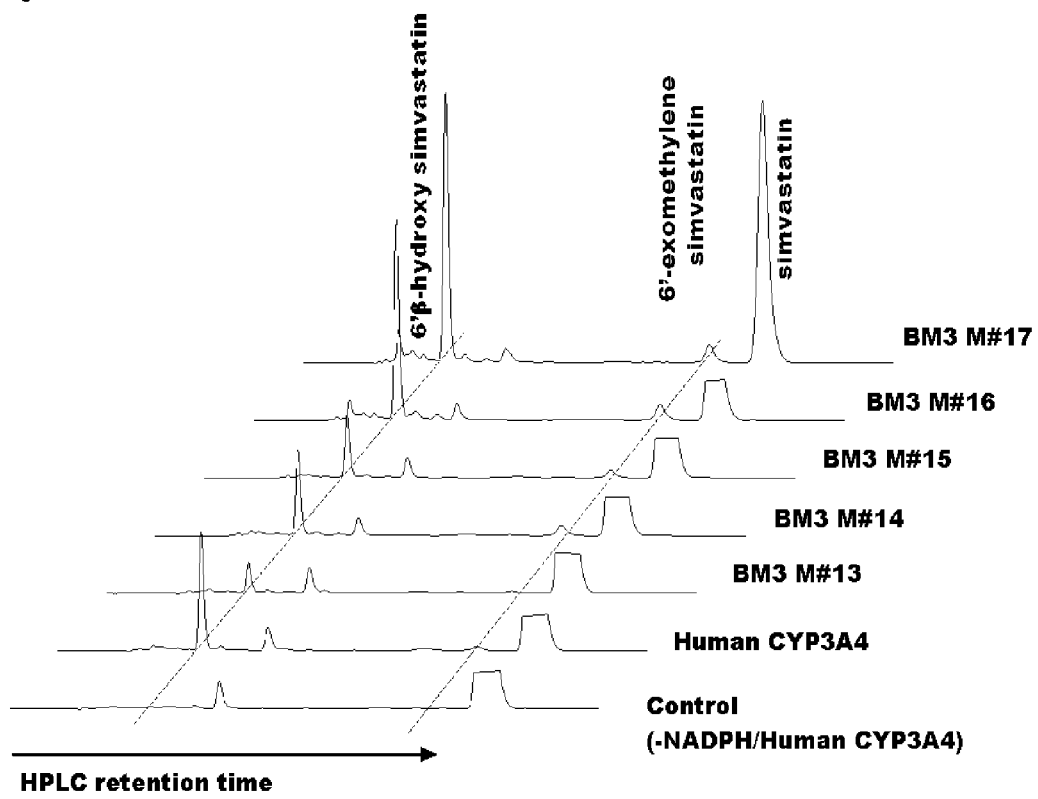
FIG. 1 shows high-performance liquid chromatography (HPLC) chromatograms of simvastatin metabolites produced by CYP102A1 mutants (M#13 to M#17) and human CYP3A4.
Figure 2:
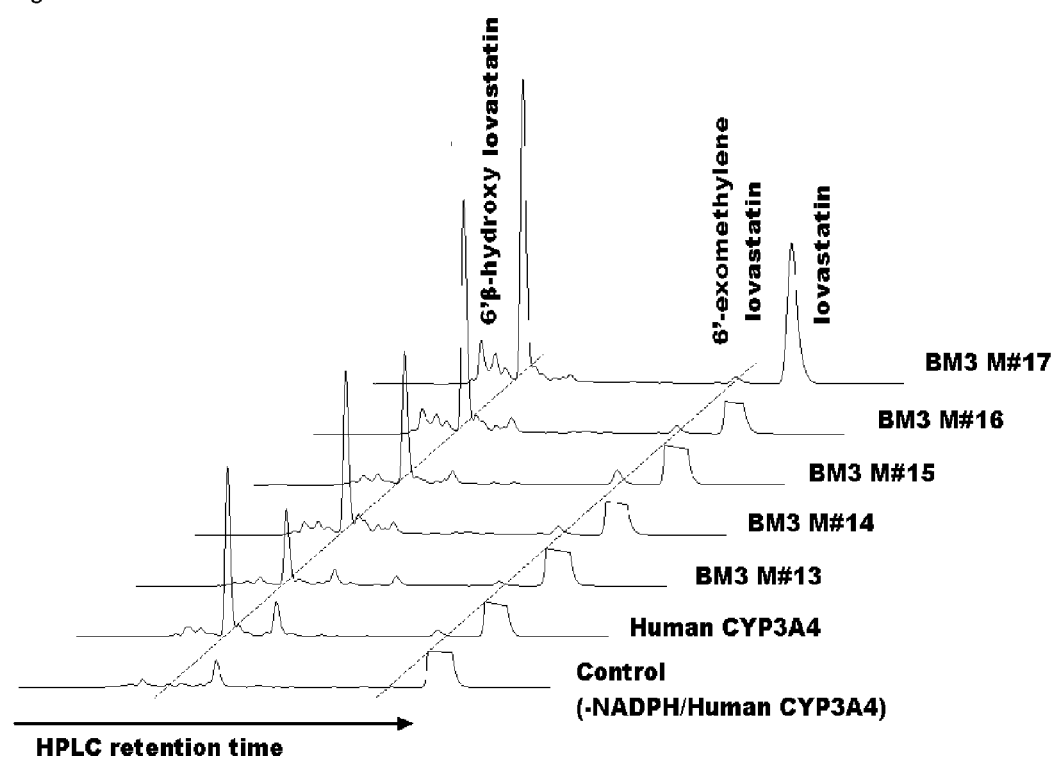
FIG. 2 shows HPLC chromatograms of lovastatin metabolites produced by bacterial CYP102A1 mutants (#13 to #17) and human CYP3A4.

First, the ability of wild-type and a set of P450 BM3 mutants to oxidize simvastatin and lovastatin was measured at a fixed substrate concentration (100 μM). While simvastatin and lovastatin are known to produce at least four and three metabolites, respectively, CYP102A1 mutants produced only two metabolites, one major (6β-OH statin) and one minor (6'-exomethylene statin) metabolites. The metabolites were analyzed by HPLC and compared to those of human CYP3A4 (FIGS. 1 and 2). Since there is no need to comprise a separate step of the 6'β-OH statin and 6'-exomethylene statin from other products, the use of wild-type and mutant CYP102A1 is beneficial.

Example 3-2

LC-MS Analysis

For the identification of simvastatin and lovastatin metabolites, produced by P450 BM3 mutants, LC-MS analysis was conducted by comparing LC profiles and fragmentation patterns of simvastatin and lovastatin metabolites.

CYP102A1 mutants and human CYP3A4 were incubated with 100 μM of lovastatin or simvastatin at 37° C. for 30 min in the presence of an NADPH-generating system. Reactions were terminated by the addition of 2-fold ice-cold $CH_2Cl_2$. After centrifugation, the supernatant from each incubation was removed and evaporated to dryness. The reaction residue was reconstituted into 100 μl of mobile phase by vortex mixing and sonication for 20 sec. An aliquot (10 μl) of this solution was injected onto the LC column. LC-MS analysis was carried out on Shimadzu LCMS-2010 EV system (Shimadzu Corporation, Japan) having LCMS solution software in electro spray ionization (positive) mode. The separation was performed on a Shim-pack VP-ODS column (2.0 mm i.d.×250 mm, Shimadzu Corporation, Japan) using a mobile phase of acetonitrile and water (70:30, v/v) containing 2.5 mM formic acid at a flow rate of 0.16 ml/min. To identify the metabolites, mass spectra were recorded by electro spray ionization in positive mode. Interface and detector voltages are 4.4 kV and 1.5 kV, respectively. Nebulization gas flow was set at 1.5 l/min. Interface, curve desolvation line (CDL), and heat block temperatures are 250, 230, and 200° C., respectively.

Figure 3B:
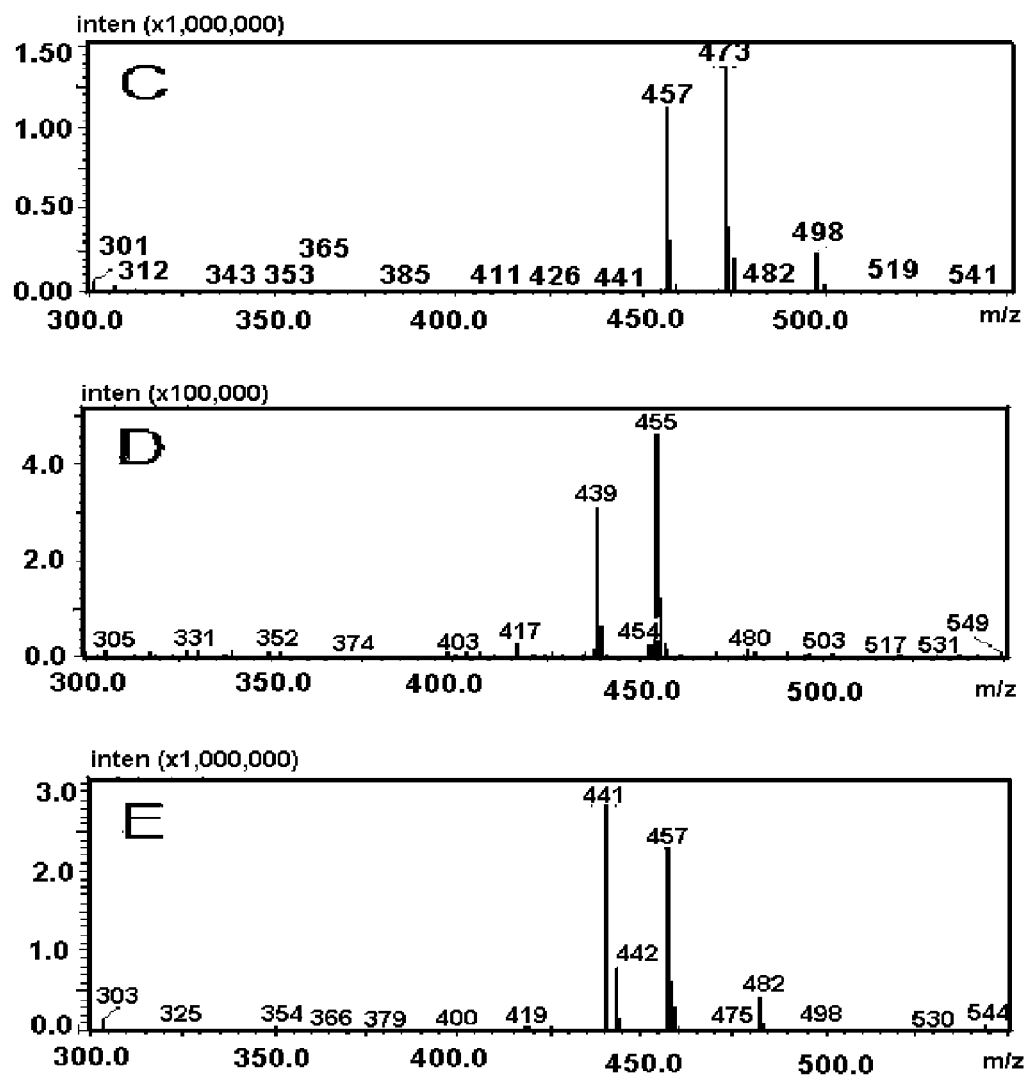
Figure 3C:
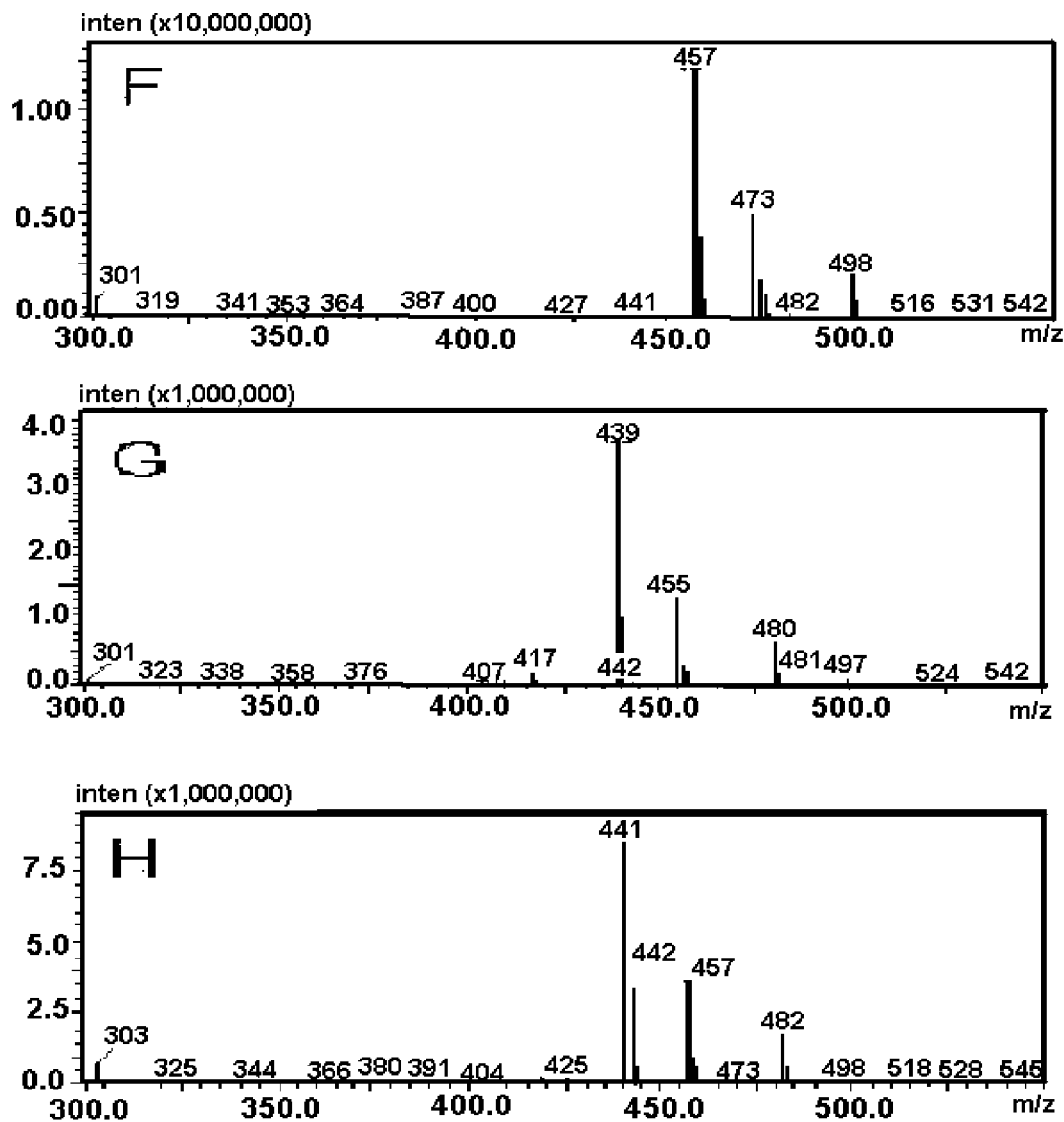

FIG. 3a to FIG. 3c show LC-MS elution profiles of simvastatin and its metabolites produced by CYP102A1 mutant #17 and human CYP3A4. TIC (total ion current) profiles of the metabolites generated by human CYP3A4 (A) and CYP102A1 mutant #17 (B) are shown. The profile of the reaction samples showed peaks at 5.433 min (6'β-hydroxyl simvastatin), 14.933 min (6'-exomethylene simvastatin), and 17.100 min (simvastatin). Main peaks in mass spectra of 6'β-hydroxylated simbastatin (C and F), 6'-exomethylene simvastatin (D and G), and simvastatin (E and H) produced by human CYP3A4 (C, D, and E) and CYP102A1 mutant #17 (F, G, and H), were observed at 457, 439, and 441, respectively when calculated as $[M+Na]^+$.

Figure 4B:
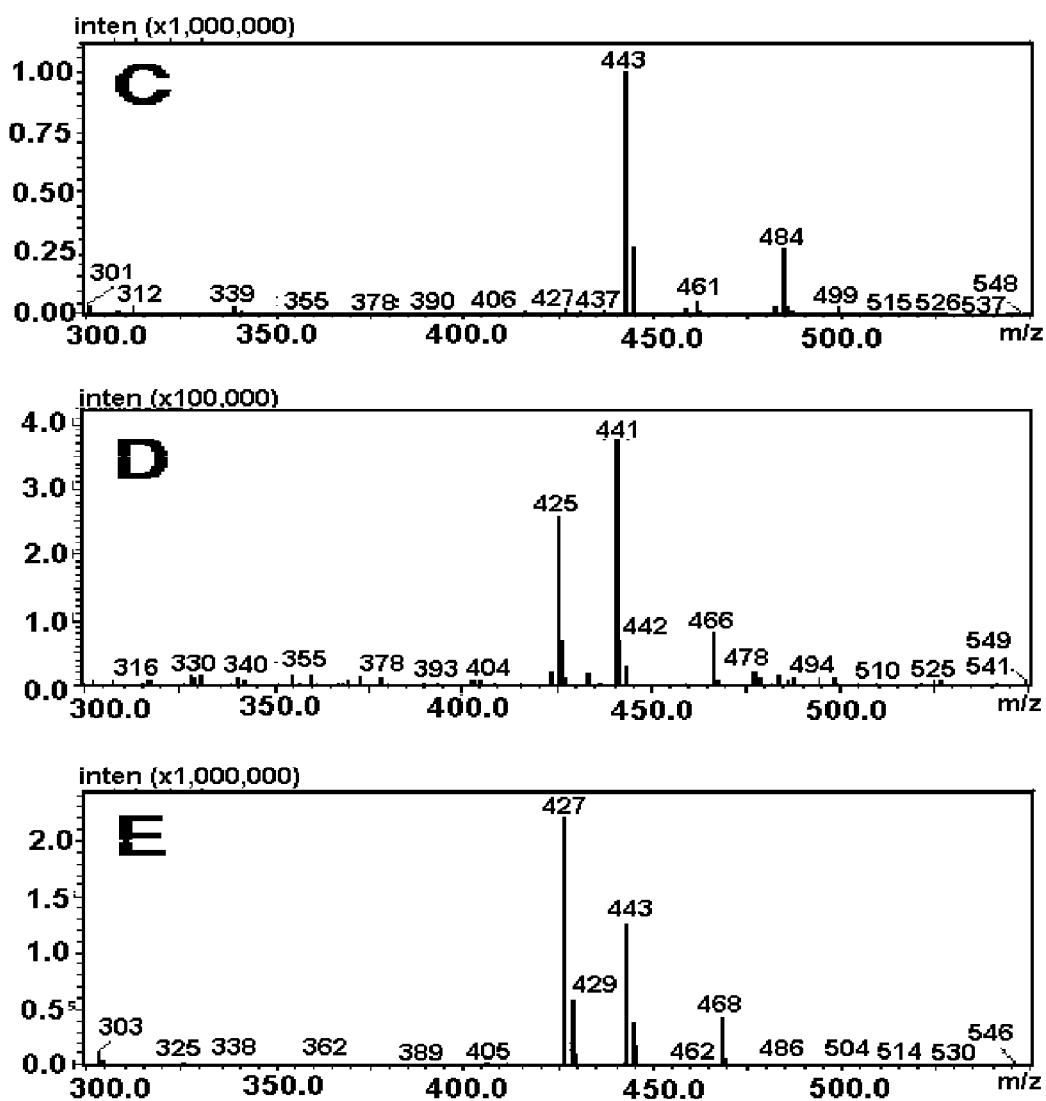
Figure 4C:
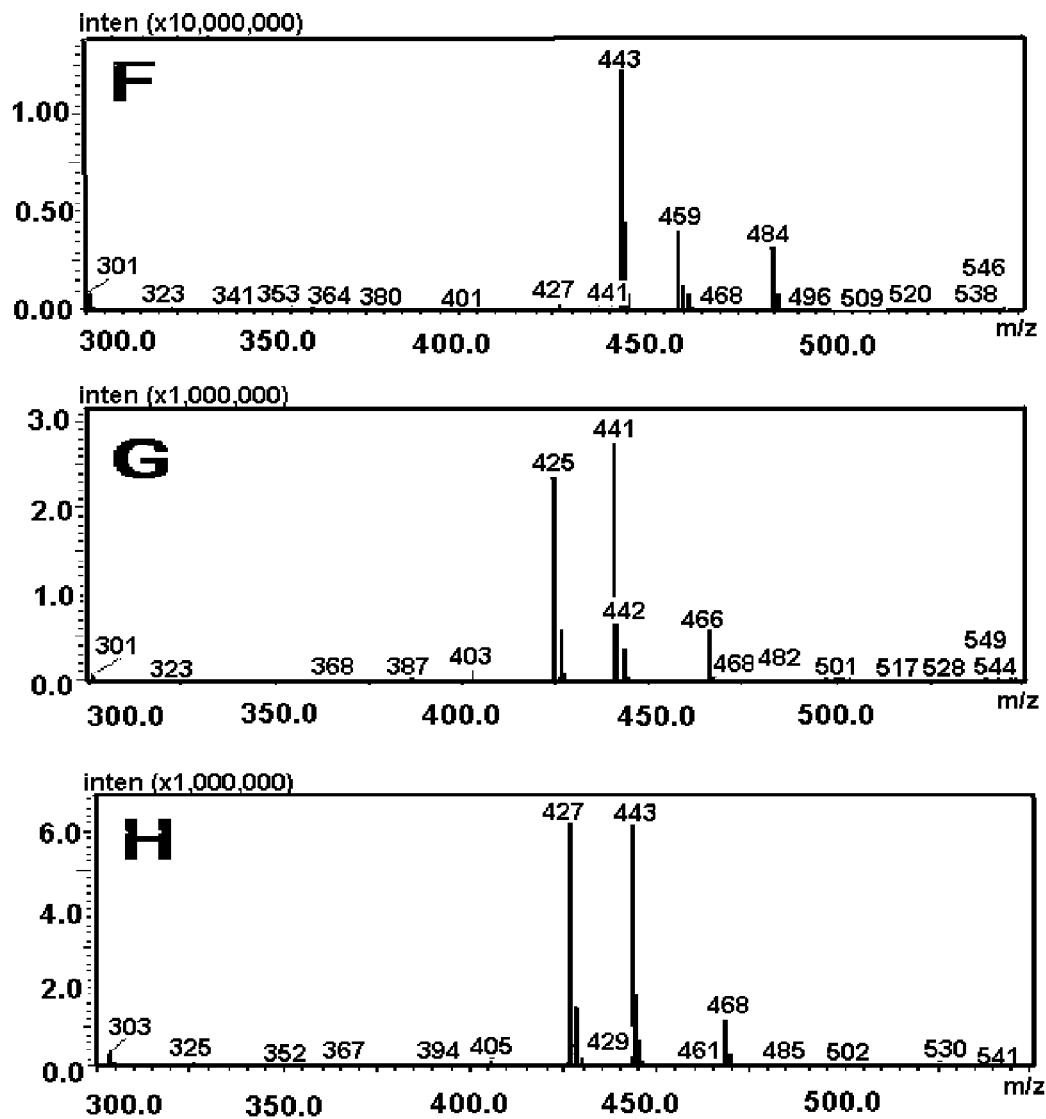

FIG. 4a to FIG. 4c show LC-MS elution profile of lovastatin and its metabolites produced by CYP102A1 mutant #17 and human CYP3A4. TIC profiles of the metabolites generated by human CYP3A4 (A) and CYP102A1 mutant #17 (B) are shown. The profile of the reaction samples showed peaks at 4.933 min (6'β-hydroxyl lovastatin), 11.367 min (6'-exomethylene lovastatin), and 13.267 min (lovastatin). The peaks in mass spectra of 6'β-hydroxylation (C and F), 6-exomethylene (D and G), and lovastatin (E and H) product by human CYP3A4 (C, D, and E) and CYP102A1 mutant #17 (F, G, and H), were observed at 443, 425, and 427, respectively, when calculated as $[M+Na]^+$.

Based on the LC-MS analysis of the reactants, the production of 6'β-OH statin and 6'-exomethylene statin by CYP102A1 mutants was identified. The retention time and fragmentation pattern of the metabolites produced by CYP102A1 mutants were exactly matched to those of authentic metabolites produced by human CYP3A4.

Example 3-3

Absorption Spectrum Analysis

For the identification of simvastatin and lovastatin metabolites, produced by P450 BM3 mutants, absorption spectra of simvastatin and lovastatin metabolites produced by P450 BM3 mutants were compared with those produced by human CYP3A4. It was identified the absorption spectra were exactly matched to each other.

Figure 5:
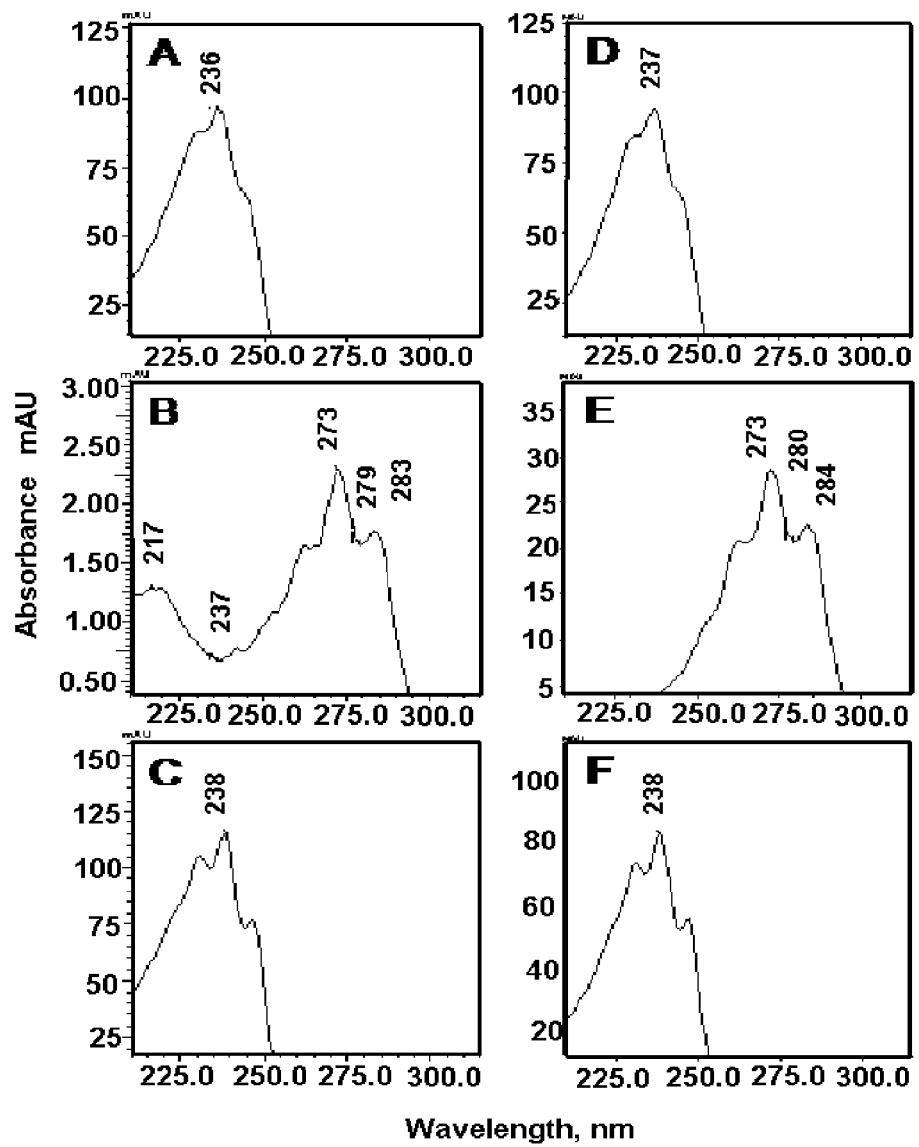
FIG. 5 shows absorption spectra of simvastatin and its metabolites produced by human CYP3A4 (A, B, and C) and CYP102A1 mutant #17 (D, E, and F). A and D represent 6'β-hydroxyl simvastatin; B and E represent 6'-exomethylene simvastatin; and C and F represent simvastatin.

FIG. 5 shows absorption spectra of simvastatin and its metabolites by human CYP3A4 (A, B, and C) and CYP102A1 mutant #17 (D, E, and F). The spectra were recorded in the mobile phase composition at which they eluted from the column. A and D represent 6'β-hydroxyl simvastatin; B and E represent 6'-exomethylene simvastatin; and C and F represent simvastatin.

Figure 6:
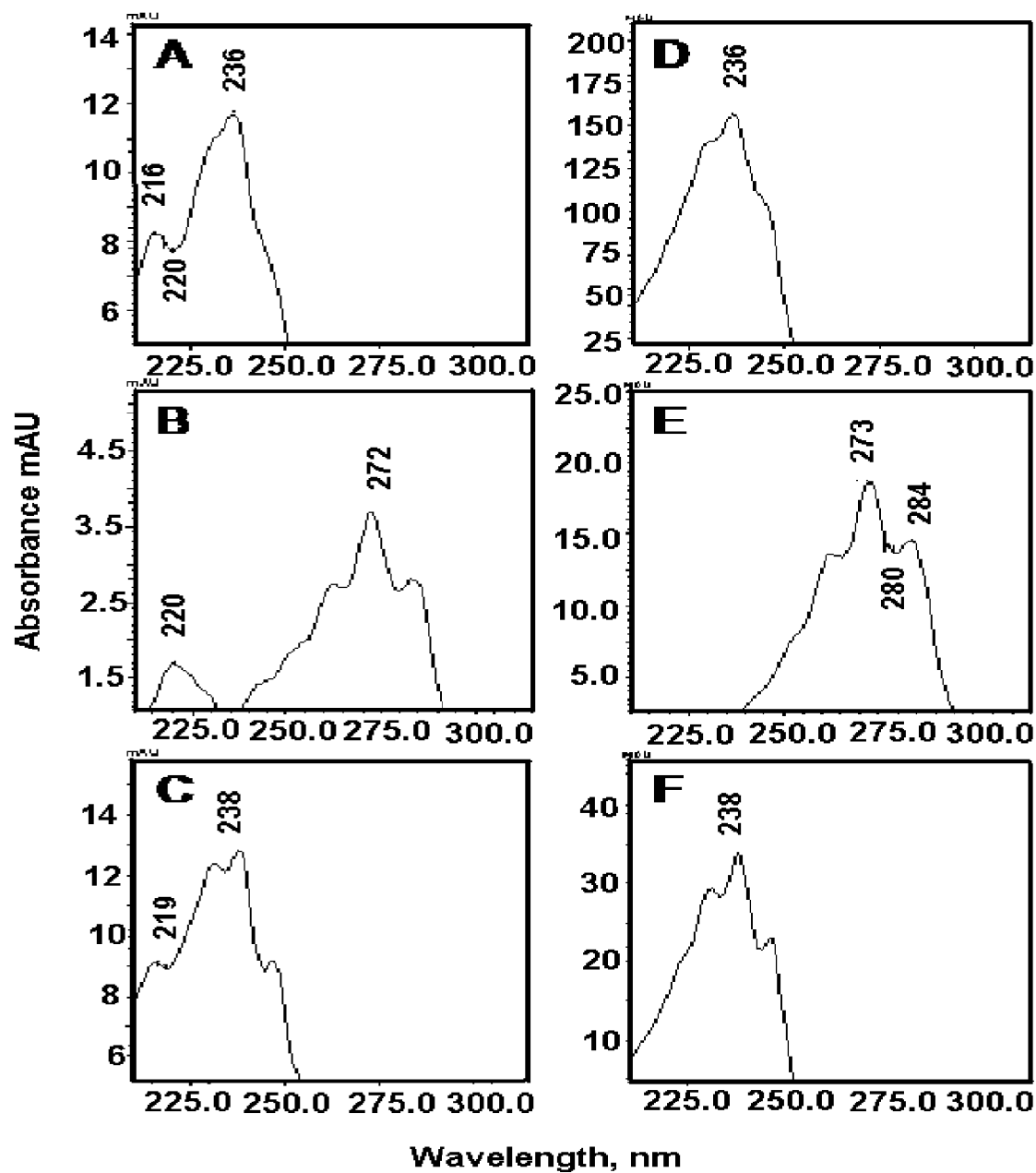
FIG. 6 shows absorption spectra of lovastatin and its metabolites produced by human CYP3A4 (A, B, and C) and CYP102A1 mutant #17 (D, E, and F). A and D represent 6'β-hydroxyl lovastatin; B and E represent 6'-exomethylene lovastatin; and C and F represent lovastatin.

FIG. 6 shows absorption spectra of lovastatin and its metabolites by human CYP3A4 (A, B, and C) and CYP102A1 mutant #17 (D, E, and F). The spectra were recorded in the mobile phase composition at which they eluted from the column. A and D represent 6'β-hydroxyl lovastatin; B and E represent 6'-exomethylene lovastatin; and C and F represent lovastatin.

Example 3-4

NMR Analysis

An Agilent model 1100 HPLC system was used for the isolation of the 6'β-OH metabolites of simvastatin and lovastatin in the reaction mixtures. Semi-preparative columns were used for the isolation of 6'β-OH simvastatin (Waters Sunfire Prep C18, 5 μm, 10 mm i.d.×150 mm) and 6'β-OH lovastatin (Varian Pursuit 5 C18, 5 μm, 10 mm i.d.×250 mm) from the mixtures. The 6'β-OH simvastatin was eluted with a linear gradient (1.5%/min) of 30-90% $CH_3CN$ after elution of 30% $CH_3CN$ for 10 min. The metabolite fractions were collected at 18.2 min. The 6'β-OH lovastatin was eluted with a series of gradients: $H_2O$: $CH_3CN$ (75:25, v/v) for 20 min; (0.5%/min) of 25-45% $CH_3CN$ for 40 min; (4.5%/min) of 45-90% $CH_3CN$ for 40 min; 90% $CH_3CN$ for 10 min. The metabolite fractions were collected at 63.7 min. The flow rate was 3 ml/min for both columns and the eluates were monitored at 240 nm.

NMR experiments were performed using a Varian VNMRS 600 MHz NMR spectrometer equipped with a carbon-enhanced cryogenic probe. Chloroform-dl was used as a solvent, and chemical shifts for proton and carbon were measured in parts per million (ppm) relative to TMS. All of the one-dimensional (1D) and two-dimensional (2D) NMR experiments were performed with standard pulse sequences in VNMR (v. 2.3) library and processed with the same software. Spectral assignments were done with 2D'H-, $^{13}$C-NMR spectroscopy along with 2D NMR spectroscopic techniques (DQ-COSY, HSQC, HMBC). The stereochemical configurations of 6'β-OH position of both compounds were determined with 1-demensional NOESY.

Table 3 shows chemical structures of simbastatin (top left), 6'β-OH simvastatin (top right), lovastatin (bottom left), and 6'β-OH lovastatin (bottom right) for the NMR assignment.

TABLE 3

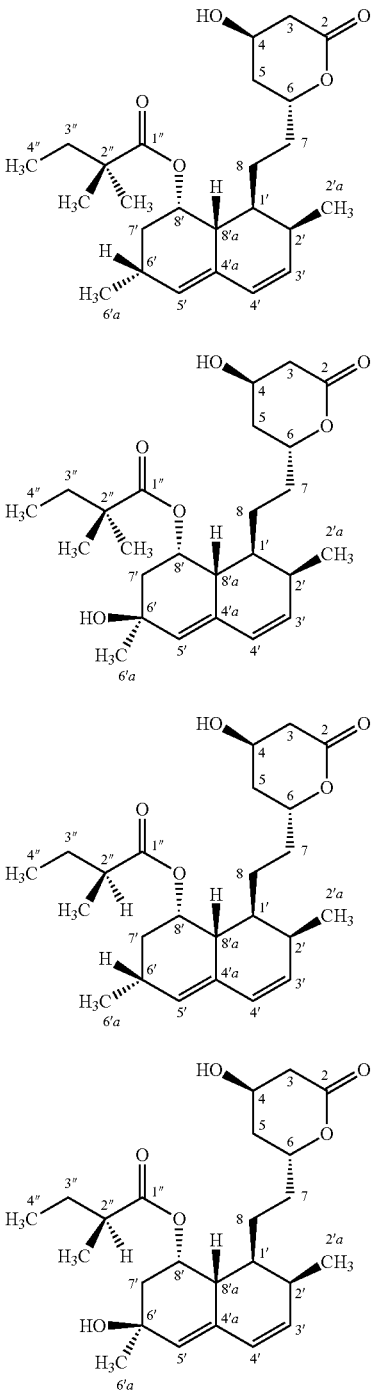

The results of NMR spectroscopy analysis are shown in Tables 4 to 7. The stereochemical configurations of 6'β-OH position of both compounds were determined with ID NOESY.

TABLE 4

Chemical shifts of Simvastatin(ppm, CDCl3)
Simvastatin(Sim-6)

| | 13C | 1H | HMBC(H→C) |
|---|---|---|---|
| 1'-CH | 36.59 | 1.68 | C-8'a, C-2' |
| 2'-CH | 30.61 | 2.37 | CH3-2'a, C-3', C-4', C-1', C-8'a |
| 3'-CH | 132.84 | 5.79 | C-4'a, C-1', C-2' CH3-2'a |
| 4'-CH | 128.37 | 5.99 | C-5', C-8'a, C-2' |
| 5'-CH | 129.72 | 5.51 | C-6', C-8'a, C-7', C-4' |
| 6'-CH | 27.25 | 2.44 | |
| 7'-CH2 | 32.86 | 2.44, 1.95 | CH3-6'a, C-5'(weak, check), C-8', C-8a' |
| 8'-CH | 67.92 | 5.37 | C-6', C-4'a |
| 8'a-CH | 37.49 | 2.26 | C-2', C-1'(weak) |
| 3-CH2 | 38.59 | 2.74, 2.62 | C-2, C-4 |
| 4-CH | 62.75 | 4.38 | |
| 5-CH2 | 36.21 | 1.98, 1.69 | C-6 |
| 6-CH | 76.24 | 4.61 | |
| 7-CH2 | 32.94 | 1.89, 1.28 | C-8, C-6, C-1' |
| 8-CH2 | 24.29 | 1.49, 1.37 | C-7, C-6, C-1', C-2' |
| 3"-CH2 | 32.99 | 1.56 | CH3-2", C-1"(carbonyl), C-4", C-2"(q) |
| 4"-CH3 | 9.33 | 0.83 | C-3", C-2"(q) |
| 2'a-CH3 | 13.87 | 0.89 | C-2' |
| 6'a-CH3 | 23.03 | 1.08 | C-7' |
| 2"-CH3(2ea) | 24.79, 24.75 | 1.27, 1.13 | C-3", C-1"(carbonyl), C-2"(q) |
| 2"(quarternary C) | 42.99 | x | |
| 4'a(quarternary C) | 131.47 | x | |
| 2(Carbonyl) | 170.06 | x | |
| 1"(Carbonyl) | 177.80 | x | |

TABLE 5

Chemical shifts of
6'-beta-hydroxy-Simvastatin(ppm, CDCl3)
6'-beta-hydroxy-Simvastatin

| | 13C | 1H | HMBC(H→C) |
|---|---|---|---|
| 1'-CH | 36.32 | 1.67 | |
| 2'-CH | 30.71 | 2.41 | C-3', C-4' C-8'a, CH3-2'a |
| 3'-CH | 135.79 | 5.91 | C-4'a, C-1', C-2' |
| 4'-CH | 127.68 | 5.99 | C-4'a, C-5', C-8'a, C-2' |
| 5'-CH | 129.65 | 5.45 | C-4', C-7' C-8'a |
| 6'-CH | 68.65 | x | |
| 7'-CH2 | 42.40 | 2.44, 1.93 | C-6', CH3-6'a |
| 8'-CH | 69.19 | 5.40 | C-4'a |
| 8'a-CH | 37.62 | 2.34 | |
| 3-CH2 | 38.62 | 2.75, 2.63 | C-2(carbonyl), C-4 |
| 4-CH | 64.79 | 4.39 | |
| 5-CH2 | 36.20 | 1.96, 1.69 | |
| 6-CH | 76.04 | 4.61 | |
| 7-CH2 | 32.76 | 1.88, 1.28 | C-6, C-5 |
| 8-CH2 | 24.09 | 1.42 | C-6, C-1', C-7 |
| 3"-CH2 | 33.03 | 1.56 | C-1"(carbonyl), C-2", C-3", CH3-2", CH3-4" |
| 4"-CH3 | 9.32 | 0.84 | C-2" |
| 2'a-CH3 | 13.57 | 0.89 | C-3', C-1', C-2' |
| 6'a-CH3 | 30.78 | 1.35 | C-5', C-6', C-7' |
| 2"-CH3(2ea) | 24.78, 24.76 | 1.14, 1.13 | C-1"(carbonyl), C-2", C-3" |
| 2"(quarternary C) | 43.07 | x | |
| 4'a(quarternary C) | 133.50 | x | |
| 2(Carbonyl) | 169.88 | x | |
| 1"(Carbonyl) | 177.50 | x | |

TABLE 6

Chemical shifts of Lovastatin(ppm, CDCl3)
Lovastatin

| | 13C | 1H | HMBC(H→C) |
|---|---|---|---|
| 1'-CH | 36.53 | 1.70 | C-8'a, C-2', CH3-2'a |
| 2'-CH | 30.61 | 2.38 | C-3', C-4', C-8'a, CH3-2'a |
| 3'-CH | 133.05 | 5.79 | C-4'a, C-1', C-2', CH3-2'a |
| 4'-CH | 128.25 | 6.00 | C-4'a, C-5', C-8'a, C-2', CH3-2'a |
| 5'-CH | 129.58 | 5.53 | C-4', C-8'a, C-7', C-6' |
| 6'-CH | 27.39 | 2.45 | C-4'a(?), C-8', CH3-6'a |
| 7'-CH2 | 32.59 | 1.92 | C-5', C-8'a, C-6', CH3-6'a, C-8' |
| 8'-CH | 67.85 | 5.39 | C-4'a, C-6' |
| 8'a-CH | 37.20 | 2.27 | C-4'a |
| 3-CH2 | 38.52 | 2.73, 2.63 | C-2(carbonyl), C-4, C-5 |
| 4-CH | 62.52 | 4.37 | |
| 5-CH2 | 36.04 | 1.68, 1.97 | C-6, C-4 |
| 6-CH | 76.37 | 4.62 | |
| 7-CH2 | 32.88 | 1.87, 1.29 | C-6, C-1', C-8, C-5 |
| 8-CH2 | 24.23 | 1.51, 1.39 | C-6, C-1', C-7, C-2' |
| 3"-CH2 | 26.79 | 1.66, 1.44 | C-1", C-2", CH3-2", CH3-4" |
| 4"-CH3 | 11.71 | 0.88 | C-2", C-3" |
| 2'a-CH3 | 13.83 | 0.90 | 3', 1', 2' |
| 6'a-CH3 | 22.79 | 1.08 | 5', 7', 6' |
| 2"-CH3(lea) | 16.22 | 1.11 | C-1", C-2", C-3", |
| 2"-CH | 41.46 | 2.35 | C-1", C-3", CH3-2", CH3-4" |
| 4'a(quarternary C) | 131.51 | x | |
| 2(Carbonyl) | 170.52 | x | |
| 1"(Carbonyl) | 176.92 | x | |

TABLE 7

Chemical shifts of
6'-beta-hydroxy-Lovastatin(ppm, CDCl3)
6'-beta-hydroxy-Lovastatin

| | 13C | 1H | HMBC(H→C) |
|---|---|---|---|
| 1'-CH | 36.19 | 1.69 | CH3-2'a |
| 2'-CH | 30.57 | 2.40 | C-3', C-4', C-1', CH3-2'a |
| 3'-CH | 135.90 | 5.92 | C-4'a, C-1', C-2'(weak) |
| 4'-CH | 127.61 | 5.99 | C-4'a, C-5', C-8'a |
| 5'-CH | 129.68 | 5.46 | C-4', C-7', C-8'a |
| 6'-CH | 68.79 | x | |
| 7'-CH2 | 42.19 | 2.43, 1.90 | C'6, CH3-6'a |
| 8'-CH | 68.85 | 5.42 | |
| 8'a-CH | 37.42 | 2.33 | |
| 3-CH2 | 38.61 | 2.74, 2.62 | C-2(carbonyl) |
| 4-CH | 62.80 | 4.38 | |
| 5-CH2 | 36.27 | 1.94, 1.67 | |
| 6-CH | 75.99 | 4.61 | |
| 7-CH2 | 32.74 | 1.87, 1.28 | C-6 |
| 8-CH2 | 24.03 | 1.45 | |
| 3"-CH2 | 26.85 | 1.66, 1.46 | C-1"(carbonyl), C-2", CH3-2", CH3-4" |
| 4"-CH3 | 11.74 | 0.89 | C-2", C-3" |
| 2'a-CH3 | 13.59 | 0.90 | C3', C-1', C-2' |
| 6'a-CH3 | 30.74 | 1.34 | C-5', C-7', C-2' |
| 2"-CH3(lea) | 16.29 | 1.12 | C-1"(carbonyl), C-2", C-3" |
| 2"-CH | 41.40 | 2.37 | C-1"(carbonyl), CH3-2", CH3-4" |
| 4'a(quarternary C) | 133.50 | x | |
| 2(Carbonyl) | 169.99 | x | |
| 1"(Carbonyl) | 176.17 | x | |

Example 3-5

Determination of Turnover Number

Table 8 shows the formation rate of 6'β-OH products generated by 17 types of CYP102A1 mutants. Assays were performed using 100 μM simvastatin or lovastatin. Values are the mean±SD of triplicate determinations.

TABLE 8

| | nmol product/min/nmol P450 | | | |
|---|---|---|---|---|
| | Simvastatin | | Lovastatin | |
| Enzyme | 6β'-OH | 6'-Exomethylene | 6β'-OH | 6'-Exomethylene |
| Human C3A4 | 3.0 ± 0.1 | 0.22 ± 0.01 | 6.5 ± 0.3 | 0.43 ± 0.01 |
| BM3 WT | 0.0049 ± 0.0017 | N.D. | N.D. | N.D. |
| Mutant | | | | |
| #1 | 0.020 ± 0.002 | N.D. | 0.043 ± 0.005 | N.D. |
| #2 | 0.0043 ± 0.0005 | 0.0013 ± 0.0006 | N.D. | N.D. |
| #3 | 0.028 ± 0.003 | 0.0056 ± 0.0030 | 0.20 ± 0.01 | N.D. |
| #4 | N.D. | N.D. | N.D. | N.D. |
| #5 | 0.0024 ± 0.0010 | 0.0019 ± 0.0003 | N.D. | N.D. |
| #6 | N.D. | N.D. | 0.063 ± 0.049 | N.D. |
| #7 | 0.025 ± 0.012 | 0.00033 ± 0.00053 | 0.14 ± 0.02 | N.D. |
| #8 | 0.29 ± 0.02 | N.D. | 0.40 ± 0.03 | 0.084 ± 0.007 |
| #9 | 0.077 ± 0.003 | 0.0036 ± 0.0002 | 0.075 ± 0.006 | N.D. |
| #10 | 0.046 ± 0.003 | 0.00028 ± 0.00068 | 0.22 ± 0.17 | 0.057 ± 0.008 |
| #11 | 0.67 ± 0.02 | 0.071 ± 0.005 | 0.87 ± 0.02 | 0.25 ± 0.01 |
| #12 | 0.85 ± 0.01 | 0.066 ± 0.003 | 1.5 ± 0.1 | 0.24 ± 0.01 |
| #13 | 0.82 ± 0.01 | 0.045 ± 0.003 | 2.2 ± 0.1 | 0.24 ± 0.01 |
| #14 | 2.5 ± 0.1 | 0.52 ± 0.01 | 6.1 ± 1.0 | 0.59 ± 0.03 |
| #15 | 1.9 ± 0.1 | 0.43 ± 0.01 | 3.9 ± 0.2 | 0.80 ± 0.01 |
| #16 | 8.5 ± 0.3 | 1.2 ± 0.1 | 12 ± 1 | 0.68 ± 0.03 |
| #17 | 10 ± 1 | 1.3 ± 0.1 | 18 ± 1 | 0.52 ± 0.08 |

N.D., not detectable(the rate of product formation was less than 0.001 nmol product/min/nmol P450)

The turnover numbers for the entire set of the 17 mutants for the oxidation of statins (product formation) varied over a wide range. Mutants #16 and #17 showed higher activities than that of human CYP3A4. In the case of mutant #17, its turnover number (10 min$^{-1}$) was 3.3 and 2040-fold higher than that of human CYP3A4 and wild-type CYP102A1, respectively.

Simvastatin and lovastatin proved to be a good substrate for CYP102A1 enzymes, with high turnover numbers (up to 10 and 18 min$^{-1}$ for 6'β-OH product formation of simvastatin and lovastatin, respectively, in the case of mutant #17).

Example 3-6

Determination of the Total Turnover Numbers

In order to measure the total turnover numbers (TTNs; mol product/mol catalyst) of mutant CYP102A1, total 1.0 mM statin was used. The reaction was initiated by the addition of the NADPH-generating system in the presence of 500 μM substrate and incubated at 37° C. for 4 hours. After 2 hours of incubation, the 500 μM substrate was added to the reaction mixture. The formation rate of simvastatin metabolites was determined by HPLC chromatograms.

The overall range of TTNs of the CYP102A1 mutants was 150 to 210 (Table 9 and FIG. 7).

TABLE 9

| P450 enzyme | Simvastatin | Lovastatin |
|---|---|---|
|  | nmol product/nmol P450 | |
| Human CYP3A4 | 35 ± 5 | 44 ± 6 |
| BM3 WT | 0.77 ± 0.04 | 1.9 ± 0.6 |
| BM3 M #16 | 200 ± 10 | 210 ± 10 |
| BM3 M #17 | 150 ± 10 | 200 ± 10 |

Total turnover numbers of 6'β-OH hydroxylated product formation by CYP102A1 mutants Mutant #16 showed the highest activity, which was 5~6-fold higher than that of human CYP3A4 with 4 hours of incubation.

Example 3-7

Determination of Kinetic Parameter

The kinetic parameters ($K_m$ and $k_{cat}$) were determined using nonlinear regression analysis with GraphPad PRISM software (GraphPad, San Diego, Calif.). The data was fit to the standard Michaelis-Menten equation: $v=k_{cat}[E][S]/([S]+K_m)$, where the velocity of the reaction is a function of the turnover ($k_{cat}$), which is the rate-limiting step, the enzyme concentration ([E]), substrate concentration ([S]), and the Michaelis constant ($K_m$).

Figure 8:
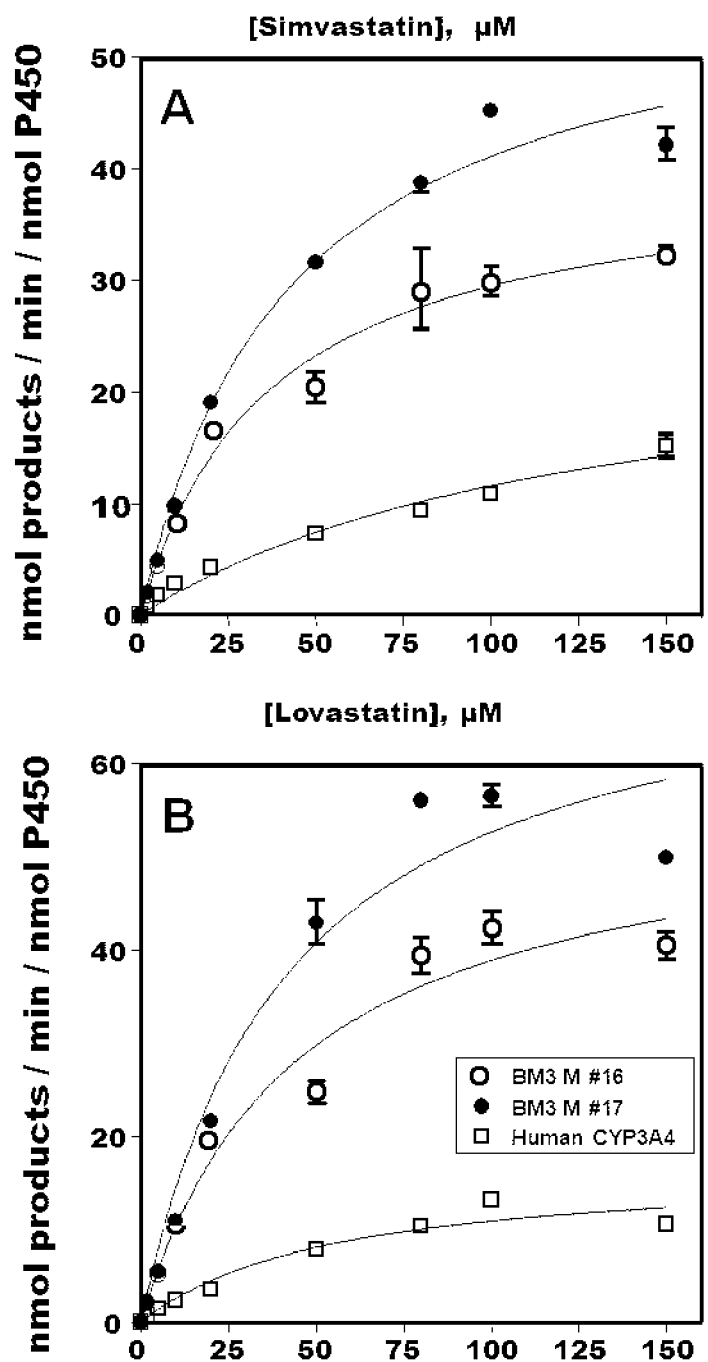
FIG. 8 shows kinetic parameters of 6'β-hydroxylation of simvastatin and lovastatin produced by CYP102A1 mutants and human CYP3A4. The 6'β-hydroxylation rates of simvastatin (A) and lovastatin (B) were measured in reaction mixtures consisting of 50 pmol CYP102A1 in 0.25 ml of 100 mM potassium phosphate buffer (pH 7.4) along with a specified amount of substrate (2 to 200 μM of statins)

Kinetic parameters of 6'β-hydroxylation of simvastatin and lovastatin by mutants #16 and 17 that have high activity were obtained (Table 10 and FIG. 8).

Kinetic Parameters of 6"β-OH Hydroxylated Product Formation by CYP102A1 Mutants

Mutants #16 and 17 showed significantly increased $K_{cat}$ value of 10 min$^{-1}$ for 6'β-hydroxylation reaction of simvastatin and lovastatin, compared to that of Human CYP3A4. Human CYP3A4 exhibited $K_{cat}$ values of 6.6 and 4.2 min$^{-1}$ for 6'β-hydroxylation reaction of simvastatin and lovastatin, respectively. The overall range of $K_m$ values of the CYP102A1 mutants was 37 to 44 μM. Human CYP3A4 exhibited a high $K_m$ value of 130 μM for 6'β-hydroxylation reaction of simvastatin. Catalytic efficiencies ($K_{cat}/K_m$) of mutant #17 for 6'β-hydroxylation reaction of simvastatin and lovastatin were 0.36 and 0.46 min$^{-1}$ μM$^{-1}$, respectively, which are 7 times or higher than that of human CYP3A4.

Example 4

Acquisition of Highly Active CYP102A1 Mutants

Highly active CYP102A1 mutants were obtained by exchanging the heme domain of natural variants with that of CYP102 mutants prepared in Example 2.

Example 4-1

Isolation and Identification of Natural Variants of CYP102A1

PCR and Cloning of Natural Variants of CYP102A1

The inventors searched and identified the natural variants of CYP102A1 by sequencing the CYP102A1 of 16 different strains of *B. megaterium*.

For DNA preparations, cells were grown in nutrient broth. After overnight growth at 37° C., the cells were centrifuged, washed, lysed, and enzymatically treated to remove RNA and protein. The DNA preparation was then treated with phenol-chloroform (50:50) and ethanol-precipitated. The purity was evaluated by measuring UV absorbance. The variant genes from *B. megaterium* were amplified by PCR using oligonucleotide primers and *B. megaterium* chromosomal DNA template. First, PCR was carried out in a 50 μl reaction mixture containing template plasmid, forward primer BamHI-F (5'-AGCGGATCCATGACAATTAAAGAAATGCCTC-3') and reverse primer SacI-R (5'-ATCGAGCTCGTAGTTTG-TAT-3'), dNTPs, and pfu polymerase. The PCR was carried out for 30 cycles consisting of 45 s of denaturation at 94° C., 45 s of annealing at 52° C., and 90 s of extension at 72° C. Next, PCR was carried out in a similar way by use of forward primer Sad-F (5'-ATACAAACTACGAGCTCGAT-3') and reverse primer XhoI-R (5'-ATCCTCGAGTTACCCAGC-CCACACGTC-3'). The PCR product was digested with BamHI and Sad, and ligated into the pCW ori expression vector that had previously digested with the same restriction enzymes. The amplified genes were subsequently cloned into the pCWBM3 BamHI/SacI vector at the BamHI/SacI restriction sites.

TABLE 10

| P450enzyme | Simvastatin | | | Lovastatin | | |
|---|---|---|---|---|---|---|
|  | $k_{cat}$ | $K_m$ | $k_{cat}/K_m$ | $k_{cat}$ | $K_m$ | $k_{cat}/K_m$ |
| BM3 M#16 | 10 ± 1 | 37 ± 6 | 0.27 ± 0.05 | 14 ± 1 | 44 ± 9 | 0.32 ± 0.07 |
| BM3 M#17 | 15 ± 1 | 42 ± 6 | 0.36 ± 0.6 | 19 ± 2 | 41 ± 9 | 0.46 ± 0.11 |
| Human CYP3A4 | 6.6 ± 0.9 | 130 ± 30 | 0.051 ± 0.014 | 4.2 ± 0.5 | 54 ± 15 | 0.078 ± 0.024 |

Because PCR amplification could lead to the introduction of random mutations and cloning of PCR products can fortuitously select the mutated sequences, CYP102A1 gene was PCR amplified a second time from genomic DNA and the sequences were directly determined without prior cloning. Exactly the same variations as those shown in Table 11 were again found, indicating that they were not artificially introduced during the PCR amplification.

Expression and Purification of Natural Variants of CYP102A1

Plasmids were transformed into *E. coli* DH5a F'-IQ cell. Overnight cultures (20 ml) grown in Luria-Bertani broth with ampicillin (100 μg/ml) selection at 37° C. were used to inoculate a 250 ml culture of Terrific broth (TB) containing 100 m/ml ampicillin, 1.0 mM thiamine, trace elements, 50 μM $FeCl_3$, 1 mM $MgCl_2$, and 2.5 mM $(NH_4)_2SO$. Cells were grown at 37° C. and 250 rpm to an $OD_{600}$ of between 0.6-0.8. Protein expression was induced by adding 1.0 mM IPTG and 1.5 mM δ-ALA, and cultures were grown at 28° C. and 200 rpm for 50 h. The cells were harvested by centrifugation (15 min, 5,000 g, 4° C.). The cell pellet was resuspended in TES buffer [100 mM Tris-HCl (pH 7.6), 500 mM sucrose, 0.5 mM EDTA)] and lysed by sonication (Sonicator, HeatSystems Ultrasonic, Inc.). After the lysate was centrifuged at 100,000 g (90 min, 4° C.), the soluble cytosolic fraction was collected and used for the activity assay. The cytosolic fraction was dialyzed against 50 mM potassium phosphate buffer (pH 7.4) and stored at −80° C. until use. The P450 concentration was determined by $Fe^{2+}$—CO versus $Fe^{2+}$ difference spectra.

Among 16 different strains of *B. megaterium*, 12 strains have natural genetic variants of CYP102A1. As some of them shared exactly the same DNA sequences, nine different types of CYP102A1 natural variants were ultimately obtained (Table 11).

TABLE 11

| | | Accession Number | | |
|---|---|---|---|---|
| Strain[a] | Variant Name[b] | Genomic DNA | 16S rRNA | 16S-23S intergenic |
| KCCM 11745 | 102A1.1 | (J04832)[c] | FJ917385 | FJ969781 |
| IFO 12108 | 102A1.1 | (J04832)[c] | FJ969756 | FJ969774 |
| ATCC 14581 | 102A1.1 | (J04832)[c] | FJ969751 | FJ969767 |
| KCCM 41415 | 102A1.1 | (J04832)[c] | FJ969762 | FJ969792 |
| KCTC 3712 | 102A1.2 | FJ899078 | FJ969764 | FJ969795 |
| KCCM 12503 | 102A1.3 | FJ899082 | FJ969761 | FJ969787 |
| ATCC 15451 | 102A1.4 | FJ899085 | FJ969753 | FJ969768 |
| ATCC 10778 | 102A1.5 | FJ899078 | FJ969746 | FJ969765 |
| KCCM 11938 | 102A1.5 | FJ899078 | FJ969760 | FJ969786 |
| KCCM 11761 | 102A1.5 | FJ899078 | FJ969757 | FJ969783 |
| KCCM 11776 | 102A1.6 | FJ899081 | FJ969758 | FJ969784 |
| KCCM 11934 | 102A1.6 | FJ899081 | FJ969759 | FJ969785 |
| ATCC 14945 | 102A1.7 | FJ899084 | FJ969749 | FJ969766 |
| ATCC 21916 | 102A1.8 | FJ899092 | FJ969755 | FJ969772 |
| KCTC 2194 | 102A1.8 | FJ859036 | FJ969763 | FJ969794 |
| ATCC 19213 | 102A1.9 | FJ899091 | FJ969754 | FJ969769 |
| ATCC 12872 | QMB1551[d] | —[e] | —[e] | —[e] |

*Bacillus megaterium* strains used in this study, and GenBank accession numbers for CYP102A1 variants, 16S rRNA, and ITS sequences between 16S-23S sequences. GenBank accession numbers (except JO4832) were assigned to nucleotide sequences determined in this study. The corresponding CYP102A1 variant gene for each strain is listed.
[a]Strains of *B. megaterium* used in this study were obtained from Korean Culture Center of Microbiology(KCCM), Korean Collection for Type Cultures(KCTC), American Type Microbiology(ATCC), and the Institute of Fermentation, Osaka(IFO).
[b]The CYP102A1 variants were named based on the amino acid similarity (Tables 12 and 13).
[c]Previously known as the nucleotide sequence of P450 BM3 (CYP102A1) from *Bacillus megaterium*.
[d]Information regarding the CYP102A1 variant of *B. megaterium* QMB1551 (ATCC12872) was obtained from the Whole Genome Sequencing of (www<dot>bios<dot>niu<dot>edu/b_megaterium/) and the variant was designated as QMB1551. We only used its genetic information to compare to those of other variants and did not study its biochemical and physical properties.
[e]Genetic information of *B. megaterium* QMB1551(ATCC12872) regarding its CYP102A1 variant, 16SrRNA, and ITS was obtained from the Whole Genome Sequencing of (www<dot>bios<dot>niu<dot>edu/b_megaterium/). Accession numbers were not provided.

The wild type CYP102A1 of *B. megaterium* was named as CYP102A1.1 and the CYP102A1 variants were named based on the amino acid similarity. Among the total 55 substituted amino acid residues of the natural variants relative to that of CYP102A1.1, substitutions of amino acids in reductase domains (residues 473-1049) (45 of 55, 82%) occurred at a much higher frequency than in heme domain (residues 1-472) (10 of 55, 18%) (Tables 12 and 13). Interestingly, no substitutions in the amino acid residues of the active site or substrate channel were seen among the 55 substitutions. Mutation of these key catalytic residues seems to be conserved during the evolution of the enzymes.

TABLE 12

Sequence variations of CYP102A1 variants

| Domain | Mutated amino acid | Change of nucleotide | *2 | *3 | *4 | *5 | *6 | *7 | *8 | *9 | QMB1551 |
|---|---|---|---|---|---|---|---|---|---|---|---|
| HD | T1P | A > C | | | | | | | | | + |
| HD | V26I | G > A | + | + | | + | + | + | + | | + |
| HD | A28T | G > A | + | + | | + | + | + | + | | + |
| HD | V127I | G > A | + | + | + | + | + | + | + | | |
| HD | A135T | G > A | + | + | | + | + | + | + | | + |
| HD | E207D | A > C | | | | + | | | | | |
| HD | A221T | G > A | | | | | | | | | + |
| HD | A295T | G > A | + | + | | | | | | | |
| HD | D369E | C > A | + | + | | | | | | | |
| HD | K452Q | A > C | | | | + | + | + | + | + | + |
| HD | T463R | T > A | | | | + | + | + | + | + | + |
| HD | V470E | A > G | | | | + | + | + | + | + | + |
| RD | K473T | G > C | | | | + | + | + | + | + | + |

TABLE 12-continued

Sequence variations of CYP102A1 variants

| Domain | Mutated amino acid | Change of nucleotide | *2 | *3 | *4 | *5 | *6 | *7 | *8 | *9 | QMB1551 |
|---|---|---|---|---|---|---|---|---|---|---|---|
| RD | A474V | C > T | + | + | + | + | + | + | + | + | + |
| RD | Q512R | G > A |   |   |   |   |   | + |   |   |   |
| RD | R525P | C > T |   |   |   |   | + |   |   |   |   |
| RD | Q546E | C > G |   |   |   |   | + | + | + | + | + |
| RD | E558D | A > C | + | + | + |   |   |   |   |   |   |
| RD | L589F | C > A |   |   |   |   |   |   | + |   |   |
| RD | A590S | G > T |   |   |   | + |   |   |   |   |   |
| RD | D599E | C > A |   |   |   | + | + | + | + | + | + |
| RD | V624L | G > T |   |   |   | + | + | + | + | + | + |
| RD | D631N | G > A |   |   |   | + |   |   |   |   |   |
| RD | D637E | T > A |   |   |   |   | + | + | + | + | + |
| RD | K639A | A > T |   |   |   | + | + | + | + | + | + |
| RD | A651S | G > T |   |   |   |   |   |   |   |   | + |
| RD | G660R | G > C |   |   |   |   | + | + | + | + | + |
| RD | T664A | A > G | + | + | + | + | + | + | + | + | + |
| RD | Q674K | C > A |   |   |   |   | + | + | + | + | + |
| RD | P675L | C > T | + | + |   |   |   |   |   |   |   |

(HD: Heme domain, RD: Reductase domain)

Variations of amino acids and nucleotides in CYP102A1 variants (*2~*9) relative to CYP102A1.1 (P450 BM3) (*1) are shown by a (+) mark. Information regarding the CYP102A1 variant (designated as QMB1551) of *B. megaterium* QMB1551(ATCC12872) was obtained from the Whole Genome Sequencing of *B. megaterium* (www<dot>bios<dot>niu<dot>edu/b_megaterium/). We only used its genetic information to compare to those of other variants. Blanks mean no change of amino acids or nucleotides.

TABLE 13

CYP102A1 Variants

| Dimain | Mutated Amino acid | Change of Nucleotide | *2 | *3 | *4 | *5 | *6 | *7 | *8 | *9 | QMB1551 |
|---|---|---|---|---|---|---|---|---|---|---|---|
| RD | A678E | C > A | + | + | + |   |   |   |   |   |   |
| RD | E687A | A > C | + | + | + |   |   |   |   |   |   |
| RD | T715A | A > G |   |   |   |   | + | + | + | + | + |
| RD | A716T | G > A |   |   |   | + | + | + | + | + | + |
| RD | A741G | C > G | + | + | + | + | + | + | + | + | + |
| RD | A782V | C > T |   |   |   |   | + | + | + | + | + |
| RD | A795T | G > A |   |   |   | + |   |   |   |   |   |
| RD | K813E | A > G | + | + | + | + | + | + | + | + | + |
| RD | I824M | A > G |   |   |   | + | + | + | + | + | + |
| RD | R825S | C > A | + | + |   |   |   |   |   |   |   |
| RD | R836H | G > A | + | + |   |   |   |   |   |   |   |
| RD | E870N | G > T | + | + | + |   | + | + | + | + | + |
| RD | I881V | A > G | + | + | + | + | + | + | + | + | + |
| RD | E887G | A > G | + | + | + | + | + | + | + | + | + |
| RD | D893G | A > G |   |   |   |   | + | + | + | + | + |
| RD | P894S | C > T | + | + | + |   |   |   |   |   |   |
| RD | G912S | C > T |   |   |   | + |   |   |   |   |   |
| RD | E947K | G > A |   |   |   |   | + | + | + | + | + |
| RD | S954N | G > A | + | + | + | + | + | + | + | + | + |
| RD | M967V | G > A | + | + | + | + | + | + | + | + |   |
| RD | Q970E | C > G |   |   |   |   | + |   |   |   |   |
| RD | M979V | A > G |   |   |   | + |   |   |   |   |   |
| RD | Q981R | A > G | + | + |   |   |   |   |   |   |   |
| RD | A1008D | C > A | + | + | + | + | + | + | + | + | + |
| RD | D1019E | C > A |   |   |   |   | + | + | + | + | + |
| RD | H1021Y | C > T | + | + | + |   |   |   |   |   |   |
| RD | Q1022K | C > G |   |   |   | + |   |   |   |   |   |
| RD | Q1022E | C > A | + | + | + |   |   |   |   |   |   |
| RD | G1039S | G > A |   |   |   | + |   |   |   |   |   |

(HD: Heme domain, RD: Reductase domain)

Example 4-2

Construction, Expression, and Purification of CYP102A1 Chimeras Derived from Reductase Domains of Natural Variants and Heme Domains of Mutants Prepared in Example 2

Combinations of heme and reductase domains were screened by an HTS system of 7-ethoxycoumarin, coumarin, phenacetin, and para-nitrophenol (p-NP), in a 96-well plate. The reaction mixtures (450 µl final reaction volume) contained 25 pmol mutant enzyme and 50 pmol natural variant enzyme, 100 mM potassium phosphate buffer (pH 7.4), an NADPH-generating system (0.5 mM NADP$^+$, 10 mM glucose 6-phosphate, and 1.0 IU glucose 6-phosphate dehydrogenase ml$^{-1}$), and the specified amount of substrate. Substrates at concentrations of 1.0 mM, 1.0 mM, 500 µM, and 1.0 mM for 7-ethoxyresorufin, coumarin, p-NP, and phenacetin, respectively were used. The reactions were initiated by addition of a solution of an NADPH—generating system. After incubating for 30 min at 37° C., the reactions of 7-ethoxycoumarin and coumarin were terminated by addition of 100 μl of 20% trichloroacetic acid (w/v), and the mixtures were centrifuged at 3000 rpm for 5 min at 4° C. Aliquots of supernatant (50 μl) were transferred into new black 96-well plates containing 150 μl Tris-HCl (pH 9.0), and the fluorescence (Ex. 355 nm and Em. 460 nm) of these mixtures were measured in a microplate reader (Infinite M200, Tecan Trading AG, Switzerland). The reaction mixtures of p-NP were terminated by addition of 100 μL of 20% trichloroacetic acid (w/v), and the mixtures were centrifuged at 3000 rpm for 5 min at 4° C. Aliquots of supernatant (100 μl) were transferred into new 96-well plates containing 50 μl of 2M NaOH, and the hydroxylated product of p-NP was measured by a microplate reader at 510 nm. The reactions of phenacetin were quenched by addition of 500 μl Purpald solution (0.16 M in 2M NaOH), and the absorbance of the mixtures at 550 nm was measured after 30-45 min using a microplate reader. Several dimeric combinations showed higher activities than those of the parent proteins.

After combinations of the corresponding reductase domain of natural variants and the heme domain of mutants prepared in Example 2 were selected to make the chimeric proteins, the expression pCW vectors were made using BamHI/SacI and SacI/XhoI sites for the heme domain and reductase domain, respectively. All chimeras were verified by full sequencing to eliminate any possibility of mutations, insertions, or deletions. All of the chimeric proteins were expressed in *E. coli* DH5 F'-IQ cells and purified as described in *Aldrichimica Acta* 33, 28-30, 2000. Purified chimeric enzymes were characterized for human P450 enzyme activities using specific substrates.

The catalytic activities of CYP102A1 chimeric proteins of the reductase domain of the natural variant with the heme domain of highly active mutant prepared in Example 2 was determined according to the method of Example 3. Table 14 shows the catalytic activities of CYP102A1 chimeric proteins of the reductase domain of the natural variant with the heme domain of mutant prepared in Example 2, which have mutations in the active site and substrate channel. Selected combinations of natural variants (with initial V) and mutants (with initial M) used to generate chimeras are M#13V2, M#15V3, M#16V3, M#17V2 and M#17V8. Data are shown as the means±EM.

TABLE 14

| | nmol product/min/nmol P450 | | | |
|---|---|---|---|---|
| | Simvastatin | | Lovastatin | |
| chimera | 6'-OH | 6'-Exomethylene | 6'-OH | 6'-Exomethylene |
| M#13V2 | 0.45 ± 0.07 | 0.05 ± 0.01 | 0.31 ± 0.10 | 0.04 ± 0.01 |
| M#15V3 | 11 ± 1 | 1.7 ± 0.3 | 13 ± 2 | 2.1 ± 0.2 |
| M#16V2 | 39 ± 2 | 5.0 ± 0.4 | 45 ± 3 | 5.2 ± 0.4 |
| M#17V2 | 42 ± 3 | 5.6 ± 0.6 | 36 ± 2 | 4.8 ± 0.4 |
| M#17V8 | 32 ± 2 | 3.7 ± 0.3 | 36 ± 5 | 4.4 ± 0.5 |

Example 5

7,8-benzoflavone Effect on Oxidation of Statin by Mutant CYP102A1

It is known that αNF can modulate the catalytic activities of human CYP3A4 (Ueng et al., 1997). In this work, the effect of αNF on the catalytic activities of CYP102A1 mutants that had human CYP3A4 activities was examined.

Reaction mixtures consists of 50 pmol P450, 100 mM potassium phosphate buffer (pH 7.4), a NADPH-generating system, and a substrate (100 μM of simvastatin or lovastatin) in the presence of αNF (2 to 50 μM).

Figure 9:
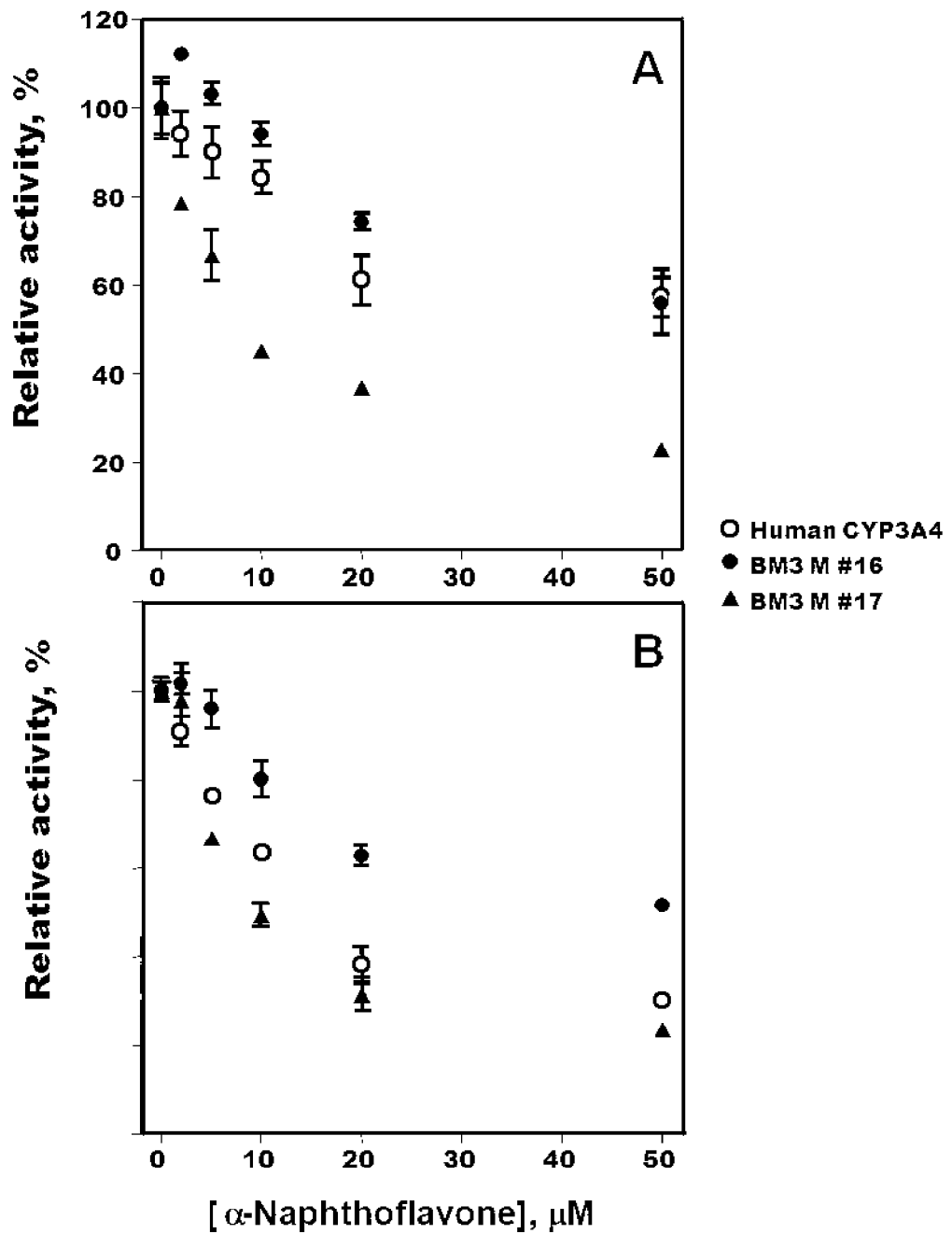
FIG. 9 shows an effect of αNF on 6'β-hydroxylation of simvastatin (A) and lovastatin (B), catalyzed by CYP102A1 mutants #16, #17, and human CYP3A4.

Products were analyzed by HPLC, as described above. In the case of human CYP3A4 activity assay, a control experiment of 50 pmol P450, 100 pmol NADPH-P450 reductase (CPR), 100 pmol cytocrhome $b_5$, and 45 μM DLPC was used instead of 50 pmol CYP102A1.

αNF inhibited the 6'β-hydroxylation of simvastatin and lovastatin in a concentration-dependent manner. When 50 μM of αNF was added to incubations with simvastatin and lovastatin (FIG. 9), the 6'β-hydroxylation activities of simvastatin and lovastatin by human CYP3A4 were inhibited by 42% and 69%, respectively. The 6'β-hydroxylation activities of simvastatin of CYP102A1 mutants #16 and #17 were inhibited by 44% and 77%, respectively. Those of lovastatin of CYP102A1 mutants #16 and #17 were inhibited by 48% and 76%, respectively, by αNF. This result shows that αNF can bind to the active site of CYP102A1 mutants to change their catalytic activities.

A triple CYP102A1 mutant of R47L/F87V/L188Q was reported to have an ability to metabolize typical mammalian P450s substrates such as amodiaquine, dextromethorphan, acetaminophen, testosterone, and 3,4-methylene dioxymethyl amphetamine (van Vugt-Lussenburg et al., 2007). Although the product formation of these chemicals by the triple CYP102A1 mutant were inhibited from 30 to 60% by αNF, αNF did not have a significant effect on the metabolism of acetaminophen and 3,4-methylenedioxymethylamphetamine.

The production of metabolites of simvastatin and lovastatin by chemical synthesis has never been reported. Therefore, an alternative to chemical synthesis of the metabolites is to use CYP102A1 enzymes to generate the metabolites of simvastatin and lovastatin.

While the present invention has been particularly shown and described with reference to exemplary embodiments thereof, it will be understood by those of ordinary skill in the art that various changes in form and details may be made therein without departing from the spirit and scope of the present invention as defined by the claims.

REFERENCES

Bernhardt R (2006) Cytochromes P450 as versatile biocatalysts. *J Biotechnol* 124: 128-145.
Capdevila J H and Falck J R (2002) Biochemical and molecular properties of the cytochrome P450 arachidonic acid monooxygenases. *Prostaglandins & Other Lipid Mediators* 68-69:325-344.
Caron G, Ermondi G, Testa B. (2007) Predicting the oxidative metabolism of statins: an application of the MetaSite algorithm. *Pharm Res.*24:480-501.
Di Nardo G, Fantuzzi A, Sideri A, Panicco P, Sassone C, Giunta C, Gilardi G (2007) Wild-type CYP102A1 as a biocatalyst: turnover of drugs usually metabolised by human liver enzymes. *J Biol Inorg Chem* 12:313-323.
Garcia M J, Reinoso R F, Sanchez Navarro A, Prous J R. (2003) Clinical pharmacokinetics of statins. *Methods Find Exp Clin Pharmacol.* 25:457-81.
Guengerich F P (2002) Cytochrome P450 enzymes in the generation of commercial products. *Nat Rev Drug Discov* 1:359-366.

Guengerich F P, Gillam E M, Shimada T (1996) New applications of bacterial systems to problems in toxicology. *Crit Rev Toxicol* 26:551-583.

Isin E M; Guengerich F P (2006) Kinetics and thermodynamics of ligand binding by cytochrome P450 3A4. *J Biol Chem* 281:9127-9136.

Johnson M D, Zuo H, Lee K H, Trebley J P, Rae J M, Weatherman R V, Desta Z, Flockhart D A, Skaar T C. (2004) Pharmacological characterization of 4-hydroxy-N-desmethyltamoxifen, a novel active metabolite of tamoxifen. *Breast Cancer Res Treat* 85:151-159.

Kim D H, Ahn T, Jung H C, Pan J G, Yun C H. (2009) Generation of the human metabolite piceatannol from the anti-cancer preventive agent resveratrol by bacterial cytochrome P450 BM3. *Drug Metab Dispos* 37:932-936

Kim D H, Kim K H, Isin E M, Guengerich F P, Chae H Z, Ahn T, Yun C H (2008a) Heterologous expression and characterization of wild-type human cytochrome P450 1A2 without conventional N-terminal modification in *Escherichia coli*. *Protein Expr Purif*. 57:188-200.

Kim D H, Kim K H, Kim D H, Liu K H, Jung H C, Pan J G, Yun C H (2008b) Generation of human metabolites of 7-ethoxycoumarin by bacterial cytochrome P450 BM3. *Drug Metab Dispos* 36:2166-2170.

Kitazume, T., Haines, D. C., Estabrook, R. W. Chen, B. & Peterson, J. A. Obligatory intermolecular electron-transfer from FAD to FMN in dimeric P450BM-3. *Bio-chemistry* 46, 11892-11901(2007).

Omura T and Sato R (1964) The carbon monoxide-binding pigment of liver microsomes. II. Solubilization, purification, and properties. *J Biol Chem* 239:2379-2385.

Park S H, Kim D H, Kim D, Kim D H, Jung H C, Pan J G, Ahn T, Kim D, Yun C H. (2010) Engineering bacterial cytochrome P450 (P450) BM3 into a prototype with human P450 enzyme activity using indigo formation. *Drug Metab Dispos* 38:732-739.

Prueksaritanont T, Subramanian R, Fang X, Ma B, Qiu Y, Lin J H, Pearson P G, Baillie T A. (2002) Glucuronidation of statins in animals and humans: a novel mechanism of statin lactonization. *Drug Metab Dispos*. 30(5):505-12.

Ruettinger, R. T., Wen, L. P. & Fulco, A. J. Coding nucleotide, 5' regulatory, and deduced amino acid sequences of P-450BM-3, a single peptide cytochrome P-450:NADPH-P-450 reductase from *Bacillus megaterium*. *J. Biol. Chem.* 264, 10987-10995(1989).

Rushmore T H, Reider P J, Slaughter D, Assang C, Shou M (2000) Bioreactor systems in drug metabolism: Synthesis of cytochrome P450-generated metabolites. *Metab Eng* 2:115-125.

Sawayama A M, Chen M M, Kulanthaivel P, Kuo M S, Hemmerle H, Arnold F H. (2009) A panel of cytochrome P450 BM3 variants to produce drug metabolites and diversify lead compounds. *Chemistry* 15:11723-11729.

Transon C, Leemann T, Dayer P. (1996) In vitro comparative inhibition profiles of major human drug metabolising cytochrome P450 isozymes (CYP2C9, CYP2D6 and CYP3A4) by HMG-CoA reductase inhibitors. *Eur J Clin Pharmacol.* 50(3):209-15.

Tornio A, Pasanen M K, Laitila J, Neuvonen P J, Backman J T. (2005) Comparison of 3-hydroxy-3-methylglutaryl coenzyme A (HMG-CoA) reductase inhibitors (statins) as inhibitors of cytochrome P450 2C8. *Basic Clin Pharmacol Toxicol.* 97(2):104-8.

Urlacher V B and Eiben S (2006) Cytochrome P450 monooxygenases: perspectives for synthetic application. *Trends Biotechnol* 24:324-330.

van Vugt-Lussenburg B M, Stjernschantz E, Lastdrager J, Oostenbrink C, Vermeulen N P and Commandeur J N (2007) Identification of critical residues in novel drug metabolizing mutants of cytochrome P450 BM3 using random mutagenesis. *J Med Chem* 50:455-461.

Vail R B, Homann M J, Hanna I, Zaks A (2005) Preparative synthesis of drug metabolites using human cytochrome P450s 3A4, 2C9 and 1A2 with NADPH-P450 reductase expressed in *Escherichia coli*. *J Ind Microbiol Biotechnol* 32:67-74.

Vickers S, Duncan C A, Chen I W, Rosegay A, Duggan D E (1990a) Metabolic disposition studies on simvastatin, a cholesterol-lowering prodrug. *Drug Metab Dispos* 18: 138-145.

Vickers S, Duncan C A, Vyas K P, Kari P H, Arison B, Prakash S R, Ramjit H G, Pitzenberger S M, Stokker G, Duggan D E (1990b) In vitro and in vivo biotransformation of simvastatin, an inhibitor of HMG CoA reductase. *Drug Metab Dispos.* 18:476-83.

Ueng Y F, Kuwabara T, Chun Y J, Guengerich F P. (1997) Cooperativity in oxidations catalyzed by cytochrome P450 3A4. *Biochemistry*.36:370-81.

Vyas K P, Kari P H, Pitzenberger S M, Halpin R A, Ramjit H G, Arison B, Murphy J S, Hoffman W F, Schwartz M S, Ulm E H, Duggan D E (1990) Biotransformation of lovastatin. I. Structure elucidation of in vitro and in vivo metabolites in the rat and mouse. *Drug Metab Dispos.* 18:203-11.

Yun C H, Kim K H, Kim D H, Jung H C and Pan J G (2007) The bacterial P450 BM3: a prototype for a biocatalyst with human P450 activities. *Trends Biotechnol* 25:289-298.

Yun C H, Yim S K, Kim D H, Ahn T (2006) Functional expression of human cytochrome P450 enzymes in *Escherichia coli*. *Curr Drug Metab* 7:411-429.

---

The invention claimed is:

1. A composition for catalyzing a reaction for preparing human metabolites of simvastatin or lovastatin, the composition comprising at least one mutant of CYP102A1 having a reductase domain and a heme domain, wherein the at least one mutant of CYP102A1 is a polypeptide having the amino acid sequence of SEQ ID NO:16 with substitutions in the reductase domain between amino acid positions 473-1048 and at least one substitution in the heme domain between amino acid positions 1-472, wherein the at least one substitution in the heme domain is selected from the group consisting of:

substituting the arginine at amino acid position 47 with alanine (A), valine (V), leucine (L), isoleucine (I), proline (P), methionine (M), phenylalanine (F) or tryptophan (W);
substituting the tyrosine at amino acid position 51 with A, V, L, I, P, M, F or W; substituting the glutamic acid at amino acid position 64 with glycine (G), serin (S), threonine (T), cysteine (C), tyrosine (Y), asparagine (N) or glutamine (Q);
substituting the alanine at amino acid position 74 with G, S, T, C, Y, N or Q;
substituting the phenylalanine at amino acid position 81 with A, V, L, I, P, M or W;
substituting the leucine at amino acid position 86 with A, V, I, P, M, F or W;
substituting the phenylalanine at amino acid position 87 with A, V, L, I, P, M or W;
substituting the glutamic acid at amino acid position 143 with G, S, T, C, Y, N or Q;
substituting the leucine at amino acid position 188 with G, S, T, C, Y, N or Q;
substituting the alanine at amino acid position 264 with G, S, T, C, Y, N or Q; and
substituting the glutamic acid at amino acid position 267 with A, V, L, I, P, M, F or W; and
wherein the at least one mutant of CYP102A1 further comprises:
substituting the alanine at amino acid position 474 with V, L, I, P, M, F or W;
substituting the glutamic acid at amino acid position 558 with aspartic acid (D);
substituting the threonine at amino acid position 664 with A, V, L, I, P, M, F or W;
substituting the proline at amino acid position 675 with A, V, L, I, M, F or W;
substituting the alanine at amino acid position 678 with glutamic acid (E) or D;
substituting the glutamic acid at amino acid position 687 with A, V, L, I, P, M, F or W;
substituting the alanine at amino acid position 741 with G, S, T, C, Y, N or Q;
substituting the lysine at amino acid position 813 with E or D;
substituting the arginine at amino acid position 825 with G, S, T, C, Y, N or Q;
substituting the arginine at amino acid position 836 with lysine (K) or histidine (H);
substituting the glutamic acid at amino acid position 870 with G, S, T, C, Y, N or Q;
substituting the isoleucine at amino acid position 881 with A, V, L, P, M, F or W;
substituting the glutamic acid at amino acid position 887 with G, S, T, C, Y, N or Q;
substituting the proline at amino acid position 894 with G, S, T, C, Y, N or Q;
substituting the serine at amino acid position 954 with G, T, C, Y, N or Q;
substituting the methionine at amino acid position 967 with A, V, L, I, P, F or W;
substituting the glutamine at amino acid position 981 with R, K or H;
substituting the alanine at amino acid position 1008 with D or E;
substituting the histidine at amino acid position 1021 with G, S, T, C, Y, N or Q; and
substituting the glutamine at amino acid position 1022 with D or E.

2. The composition of claim 1, wherein the at least one mutant of CYP102A1 comprises one or more substitutions selected from the group consisting of:
R47L/L861/F87V/L188Q/A474V/E558D/T664A/P675L/ A678E/E687A/A7410/K813E/R825S/R836H/E870N/ 1881V/E8870/P894S/S954N/M967V/Q981R/ A1008D/H1021Y/Q1022E (M#13V2);
R47L/E64G/F87V/E143G/L188Q/E267V/A474V/ E558D/T664A/P675L/A678E/E687A/A7410/K813E/ R825S/R836H/E870N/1881V/E8870/P894S/S954N/ M967V/Q981R/A1008D/H1021Y/Q1022E (M#15V3);
R47L/F81I/F87V/E143G/L188Q/E267V/A474V/E558D/ T664A/P675L/A678E/E687A/A7410/K813E/R825S/ R836H/E870N/1881V/E8870/P894S/S954N/M967V/ Q981R/A 1008D/H1021Y/Q1022E (M#16V2); and
R47L/E64G/F81I/F87V/E143G/L188Q/E267V/A474V/ E558D/T664A/P675L/A678 E/E687A/A7410/K813E/ R825S/R836H/E870N/1881V/E8870/P894S/S954N/ M967V/Q981R/A1008D/H1021Y/Q1022E (M#17V2).

3. A kit for producing human metabolites of simvastatin or lovastatin, the kit comprising the composition according to claim 1 and a NADPH-generating system.

4. A method of producing human metabolites of simvastatin or lovastatin comprising the steps of reacting the composition of claim 1 with simvastatin or lovastatin.

5. The method of claim 4, further comprising adding a NADPH-generating system to the reaction.

6. A composition for catalyzing a reaction for preparing human metabolites of simvastatin or lovastatin, the composition comprising at least one mutant of CYP102A1 having a reductase domain and a heme domain, wherein the at least one mutant of CYP102A1 is a polypeptide having the amino acid sequence of SEQ ID NO:16 with substitutions in the reductase domain between amino acid positions 473-1048 and at least one substitution in the heme domain between amino acid positions 1-472, wherein the at least one substitution in the heme domain is selected from the group consisting of:
substituting the arginine at amino acid position 47 with L;
substituting the tyrosine at amino acid position 51 with F;

substituting the glutamic acid at amino acid position 64 with G;
substituting the alanine at amino acid position 74 with G;
substituting the phenylalanine at amino acid position 81 with I;
substituting the leucine at amino acid position 86 with I;
substituting the phenylalanine at amino acid position 87 with A or V;
substituting the glutamic acid at amino acid position 143 with G;
substituting the leucine at amino acid position 188 with Q;
substituting the alanine at amino acid position 264 with G; and
substituting the glutamic acid at amino acid position 267 with V; and
wherein the at least one mutant of CYP102A1 further comprises:
substituting the alanine at amino acid position 474 with V;
substituting the glutamic acid at amino acid position 558 with D;
substituting the threonine at amino acid position 664 with A;
substituting the proline at amino acid position 675 with L;
substituting the alanine at amino acid position 678 with E;
substituting the glutamic acid at amino acid position 687 with A;
substituting the alanine at amino acid position 741 with G;
substituting the lysine at amino acid position 813 with E;
substituting the arginine at amino acid position 825 with S;
substituting the arginine at amino acid position 836 with H;
substituting the glutamic acid at amino acid position 870 with N;
substituting the isoleucine at amino acid position 881 with V;
substituting the glutamic acid at amino acid position 887 with G;
substituting the proline at amino acid position 894 with S;
substituting the serine at amino acid position 954 with N;
substituting the methionine at amino acid position 967 with V;
substituting the glutamine at amino acid position 981 with R;
substituting the alanine at amino acid position 1008 with D;
substituting the histidine at amino acid position 1021 with Y; and
substituting the glutamine at amino acid position 1022 with E.

7. A composition for catalyzing a reaction for preparing human metabolites of simvastatin or lovastatin, the composition comprising at least one mutant of CYP102A1 having a reductase domain and a heme domain, wherein the at least one mutant of CYP102A1 is a polypeptide having the amino acid sequence of SEQ ID NO:16 with substitutions in the reductase domain between amino acid positions 473-1048 and at least one substitution in the heme domain between amino acid positions 1-472, wherein the at least one substitution in the heme domain is selected from the group consisting of:
substituting the arginine at amino acid position 47 with L;
substituting the tyrosine at amino acid position 51 with F;
substituting the glutamic acid at amino acid position 64 with G;
substituting the alanine at amino acid position 74 with G;
substituting the phenylalanine at amino acid position 81 with I;
substituting the leucine at amino acid position 86 with I;
substituting the phenylalanine at amino acid position 87 with A or V;
substituting the glutamic acid at amino acid position 143 with G;
substituting the leucine at amino acid position 188 with Q;
substituting the alanine at amino acid position 264 with G; and
substituting the glutamic acid at amino acid position 267 with V; and
wherein the at least one mutant of CYP102A1 further comprises:
substituting the lysine at amino acid position 473 with T
substituting the alanine at amino acid position 474 with V;
substituting the glutamine at amino acid position 546 with E;
substituting the aspartic acid at amino acid position 599 with E;
substituting the valine at amino acid position 624 with L;
substituting the aspartic acid at amino acid position 637 with E;
substituting the lysine at amino acid position 639 with A;
substituting the glycine at amino acid position 660 with R;
substituting the threonine at amino acid position 664 with A;
substituting the glutamine at amino acid position 674 with K;
substituting the threonine at amino acid position 715 with A;
substituting the alanine at amino acid position 716 with T;
substituting the alanine at amino acid position 741 with G;
substituting the alanine acid at amino acid position 782 with V;
substituting the lysine at amino acid position 813 with E;
substituting the isoleucine at amino acid position 824 with M;
substituting the glutamic acid at amino acid position 870 with N;
substituting the isoleucine at amino acid position 881 with V;
substituting the glutamic acid at amino acid position 887 with G;
substituting the aspartic acid at amino acid position 893 with G;
substituting the glutamic acid at amino acid position 947 with K;
substituting the serine at amino acid position 954 with N;
substituting the methionine at amino acid position 967 with V;
substituting the alanine at amino acid position 1008 with D; and
substituting the aspartic acid at amino acid position 1019 with E.

8. A mutant of CYP102A1, wherein the mutant comprises substitutions selected from the group consisting of:
R47L/L86I/F87V/L188Q/A475V/E559D/T665A/P676L/A679E/E688A/A742G/K814E/R826S/R837H/E871N/I882V/E8880/P895S/S955N/M968V/Q982R/A1009D/H1022Y/Q1023E (M#13V2),
R47L/E64G/F87V/E143G/L188Q/E267V/A474V/E558D/T664A/P675L/A678E/E687A/A7410/K813E/R825S/R836H/E870N/I881V/E8870/P894S/S954N/M967V/Q981R/A1008D/H1021Y/Q1022E (M#15V3),
R47L/F81I/F87V/E143G/L188Q/E267V/A474V/E558D/T664A/P675L/A678E/E687A/A7410/K813E/

R825S/R836H/E870N/I881V/E887Q/P894S/S954N/
M967V/Q981R/A1008D/H1021Y/Q1022E
(M#16V2),
R47L/E64G/F81I/F87V/E143G/L188Q/E267V/A474V/
E558D/T664A/P675L/A678 E/E687A/A7410/K813E/
R825S/R836H/E870N/I881V/E887Q/P894S/S954N/
M967V/Q981R/A1008D/H1021Y/Q1022E
(M#17V2), and
R47L/E64G/F81I/F87V/E143G/L188Q/E267V/K474T/
A475V/Q547E/D600E/V625 L/D638E/K640A/0661R/
T665A/Q675K/T716A/A717T/A7420/A783V/K814E/
I825M/E871N/I882V/E888Q/D894G/E948K/S955N/
M968V/A1009D/D1020E (M#17V8).

9. A composition for catalyzing a reaction for preparing human metabolites of simvastatin or lovastatin, the composition comprising at least one mutant of CYP102A1 having a reductase domain and a heme domain, wherein the at least one mutant of CYP102A1 is a polypeptide having the amino acid sequence of SEQ ID NO:16 with substitutions in the reductase domain between amino acid positions 473-1048 and at least one substitution in the heme domain between amino acid positions 1-472, wherein the at least one substitution in the heme domain is selected from the group consisting of:
  substituting the arginine at amino acid position 47 with alanine (A), valine (V), leucine (L), isoleucine (I), proline (P), methionine (M), phenylalanine (F) or tryptophan (W);
  substituting the tyrosine at amino acid position 51 with A, V, L, I, P, M, F or W;
  substituting the glutamic acid at amino acid position 64 with glycine (G), serin(S), threonine (T), cysteine (C), tyrosine (Y), asparagine (N) or glutamine (Q);
  substituting the alanine at amino acid position 74 with G, S, T, C, Y, N or Q;
  substituting the phenylalanine at amino acid position 81 with A, V, L, I, P, M or W;
  substituting the leucine at amino acid position 86 with A, V, I, P, M, F or W;
  substituting the phenylalanine at amino acid position 87 with A, V, L, I, P, M or W;
  substituting the glutamic acid at amino acid position 143 with G, S, T, C, Y, N or Q;
  substituting the leucine at amino acid position 188 with G, S, T, C, Y, N or Q;
  substituting the alanine at amino acid position 264 with G, S, T, C, Y, N or Q; and
  substituting the glutamic acid at amino acid position 267 with A, V, L, I, P, M, F or W; and
wherein the at least one mutant of CYP102A1 further comprises:
  substituting the lysine at amino acid position 473 with G, S, T, C, Y, N or Q;
  substituting the alanine at amino acid position 474 with V, L, I, P, M, F or W;
  substituting the glutamine at amino acid position 546 with D or E;
  substituting the aspartic acid at amino acid position 599 with E;
  substituting the valine at amino acid position 624 with A, L, I, P, M, F or W;
  substituting the aspartic acid at amino acid position 637 with E;
  substituting the lysine at amino acid position 639 with A, V, L, I, P, M, F or W;
  substituting the glycine at amino acid position 660 with Arginine (R), K or H;
  substituting the threonine at amino acid position 664 with A, V, L, I, P, M, F or W;
  substituting the glutamine at amino acid position 674 with R, K or H;
  substituting the threonine at amino acid position 715 with A, V, L, I, P, M, F or W;
  substituting the alanine at amino acid position 716 with G, S, T, C, Y, N or Q;
  substituting the alanine at amino acid position 741 with G, S, T, C, Y, N or Q;
  substituting the alanine at amino acid position 782 with V, L, I, P, M, F or W;
  substituting the lysine at amino acid position 813 with D or E;
  substituting the isoleucine at amino acid position 824 with A, V, L, I, P, M, F or W;
  substituting the glutamic acid at amino acid position 870 with G, S, T, C, Y, N or Q;
  substituting the isoleucine at amino acid position 881 with A, V, L, P, M, F or W;
  substituting the glutamic acid at amino acid position 887 with G, S, T, C, Y, N or Q;
  substituting the aspartic acid at amino acid position 893 with G, S, T, C, Y, N or Q;
  substituting the glutamic acid at amino acid position 947 with R, K or H;
  substituting the serine at amino acid position 954 with G, T, C, Y, N or Q;
  substituting the methionine at amino acid position 967 with A, V, L, I, P, M, F or W;
  substituting the alanine at amino acid position 1008 with D or E; and
  substituting the aspartic acid at amino acid position 1019 with E.

10. The composition of claim 9, wherein the at least one mutant of CYP102A1 comprises the following substitutions:
R47L/E640/F81I/F87V/E143Q/L188Q/E267V/K473T/
A474V/Q546E/D599E/V624 L/D637E/K639A/0660R/
T664A/Q674K/T715A/A716T/A7410/A782V/K813E/
I824M/E870N/I881V/E887G/D893G/E947K/S954N/
M967V/A1008D/D1019E (M#17V8).

11. A kit for producing human metabolites of simvastatin or lovastatin, the kit comprising the composition according to claim 9 and a NADPH-generating system.

12. A method of producing human metabolites of simvastatin or lovastatin comprising the steps of reacting the composition of claim 9 with simvastatin or lovastatin.

13. The method of claim 12, further comprising adding a NADPH-generating system to the reaction.

* * * * *

SEQUENCE LISTING

<160> NUMBER OF SEQ ID NOS: 18

<210> SEQ ID NO 1
<211> LENGTH: 31
<212> TYPE: DNA
<213> ORGANISM: Artificial Sequence
<220> FEATURE:
<223> OTHER INFORMATION: primer used for the generation of mutants

<400> SEQUENCE: 1
agcggatcca tgacaattaa agaaatgcct c                                    31

<210> SEQ ID NO 2

-continued

```
<211> LENGTH: 20
<212> TYPE: DNA
<213> ORGANISM: Artificial Sequence
<220> FEATURE:
<223> OTHER INFORMATION: primer used for the generation of mutants

<400> SEQUENCE: 2
atcgagctcg tagtttgtat                                                    20

<210> SEQ ID NO 3
<211> LENGTH: 20
<212> TYPE: DNA
<213> ORGANISM: Artificial Sequence
<220> FEATURE:
<223> OTHER INFORMATION: primer used for the generation of mutants

<400> SEQUENCE: 3
gcgcctggtc tggtaacgcg                                                    20

<210> SEQ ID NO 4
<211> LENGTH: 21
<212> TYPE: DNA
<213> ORGANISM: Artificial Sequence
<220> FEATURE:
<223> OTHER INFORMATION: primer used for the generation of mutants

<400> SEQUENCE: 4
gtaacgcgct tcttatcaag t                                                  21

<210> SEQ ID NO 5
<211> LENGTH: 21
<212> TYPE: DNA
<213> ORGANISM: Artificial Sequence
<220> FEATURE:
<223> OTHER INFORMATION: primer used for the generation of mutants

<400> SEQUENCE: 5
gcatgcgatg gctcacgctt t                                                  21

<210> SEQ ID NO 6
<211> LENGTH: 25
<212> TYPE: DNA
<213> ORGANISM: Artificial Sequence
<220> FEATURE:
<223> OTHER INFORMATION: primer used for the generation of mutants

<400> SEQUENCE: 6
taagtcaagg ccttaaattt gtacg                                              25

<210> SEQ ID NO 7
<211> LENGTH: 21
<212> TYPE: DNA
<213> ORGANISM: Artificial Sequence
<220> FEATURE:
<223> OTHER INFORMATION: primer used for the generation of mutants

<400> SEQUENCE: 7
gtacgtgata ttgcaggaga c                                                  21

<210> SEQ ID NO 8
<211> LENGTH: 22
<212> TYPE: DNA
<213> ORGANISM: Artificial Sequence
<220> FEATURE:
<223> OTHER INFORMATION: primer used for the generation of mutants

<400> SEQUENCE: 8
```

```
ggagacggga tttttacaag ct                                              22

<210> SEQ ID NO 9
<211> LENGTH: 21
<212> TYPE: DNA
<213> ORGANISM: Artificial Sequence
<220> FEATURE:
<223> OTHER INFORMATION: primer used for the generation of mutants

<400> SEQUENCE: 9
gacgggttag cgacaagctg g                                               21

<210> SEQ ID NO 10
<211> LENGTH: 21
<212> TYPE: DNA
<213> ORGANISM: Artificial Sequence
<220> FEATURE:
<223> OTHER INFORMATION: primer used for the generation of mutants

<400> SEQUENCE: 10
gacgggttag tgacaagctg g                                               21

<210> SEQ ID NO 11
<211> LENGTH: 21
<212> TYPE: DNA
<213> ORGANISM: Artificial Sequence
<220> FEATURE:
<223> OTHER INFORMATION: primer used for the generation of mutants

<400> SEQUENCE: 11
gaagtaccgg gcgacatgac a                                               21

<210> SEQ ID NO 12
<211> LENGTH: 22
<212> TYPE: DNA
<213> ORGANISM: Artificial Sequence
<220> FEATURE:
<223> OTHER INFORMATION: primer used for the generation of mutants

<400> SEQUENCE: 12
atgaacaagc agcagcgagc aa                                              22

<210> SEQ ID NO 13
<211> LENGTH: 21
<212> TYPE: DNA
<213> ORGANISM: Artificial Sequence
<220> FEATURE:
<223> OTHER INFORMATION: primer used for the generation of mutants

<400> SEQUENCE: 13
ttcttaattg ggggacacgt g                                               21

<210> SEQ ID NO 14
<211> LENGTH: 22
<212> TYPE: DNA
<213> ORGANISM: Artificial Sequence
<220> FEATURE:
<223> OTHER INFORMATION: primer used for the generation of mutants

<400> SEQUENCE: 14
tgcgggacac gtgacaacaa gt                                              22

<210> SEQ ID NO 15
<211> LENGTH: 23
<212> TYPE: DNA
```

<210> SEQ ID NO 16
<211> LENGTH: 1048
<212> TYPE: PRT
<213> ORGANISM: Bacillus megaterium

<400> SEQUENCE: 16

```
Thr Ile Lys Glu Met Pro Gln Pro Lys Thr Phe Gly Glu Leu Lys Asn
  1               5                  10                  15

Leu Pro Leu Leu Asn Thr Asp Lys Pro Val Gln Ala Leu Met Lys Ile
             20                  25                  30

Ala Asp Glu Leu Gly Glu Ile Phe Lys Phe Glu Ala Pro Gly Arg Val
         35                  40                  45

Thr Arg Tyr Leu Ser Ser Gln Arg Leu Ile Lys Glu Ala Cys Asp Glu
     50                  55                  60

Ser Arg Phe Asp Lys Asn Leu Ser Gln Ala Leu Lys Phe Val Arg Asp
 65                  70                  75                  80

Phe Ala Gly Asp Gly Leu Phe Thr Ser Trp Thr His Glu Lys Asn Trp
                 85                  90                  95

Lys Lys Ala His Asn Ile Leu Leu Pro Ser Phe Ser Gln Gln Ala Met
            100                 105                 110

Lys Gly Tyr His Ala Met Met Val Asp Ile Ala Val Gln Leu Val Gln
        115                 120                 125

Lys Trp Glu Arg Leu Asn Ala Asp Glu His Ile Glu Val Pro Glu Asp
    130                 135                 140

Met Thr Arg Leu Thr Leu Asp Thr Ile Gly Leu Cys Gly Phe Asn Tyr
145                 150                 155                 160

Arg Phe Asn Ser Phe Tyr Arg Asp Gln Pro His Pro Phe Ile Thr Ser
                165                 170                 175

Met Val Arg Ala Leu Asp Glu Ala Met Asn Lys Leu Gln Arg Ala Asn
            180                 185                 190

Pro Asp Asp Pro Ala Tyr Asp Glu Asn Lys Arg Gln Phe Gln Glu Asp
        195                 200                 205

Ile Lys Val Met Asn Asp Leu Val Asp Lys Ile Ile Ala Asp Arg Lys
    210                 215                 220

Ala Ser Gly Glu Gln Ser Asp Asp Leu Leu Thr His Met Leu Asn Gly
225                 230                 235                 240

Lys Asp Pro Glu Thr Gly Glu Pro Leu Asp Asp Glu Asn Ile Arg Tyr
                245                 250                 255

Gln Ile Ile Thr Phe Leu Ile Ala Gly His Glu Thr Thr Ser Gly Leu
            260                 265                 270

Leu Ser Phe Ala Leu Tyr Phe Leu Val Lys Asn Pro His Val Leu Gln
        275                 280                 285

Lys Ala Ala Glu Glu Ala Ala Arg Val Leu Val Asp Pro Val Pro Ser
    290                 295                 300

Tyr Lys Gln Val Lys Gln Leu Lys Tyr Val Gly Met Val Leu Asn Glu
305                 310                 315                 320

Ala Leu Arg Leu Trp Pro Thr Ala Pro Ala Phe Ser Leu Tyr Ala Lys
                325                 330                 335
```

```
Glu Asp Thr Val Leu Gly Gly Glu Tyr Pro Leu Glu Lys Gly Asp Glu
            340                 345                 350

Leu Met Val Leu Ile Pro Gln Leu His Arg Asp Lys Thr Ile Trp Gly
        355                 360                 365

Asp Asp Val Glu Glu Phe Arg Pro Glu Arg Phe Glu Asn Pro Ser Ala
    370                 375                 380

Ile Pro Gln His Ala Phe Lys Pro Phe Gly Asn Gly Gln Arg Ala Cys
385                 390                 395                 400

Ile Gly Gln Gln Phe Ala Leu His Glu Ala Thr Leu Val Leu Gly Met
                405                 410                 415

Met Leu Lys His Phe Asp Phe Glu Asp His Thr Asn Tyr Glu Leu Asp
            420                 425                 430

Ile Lys Glu Thr Leu Thr Leu Lys Pro Glu Gly Phe Val Val Lys Ala
        435                 440                 445

Lys Ser Lys Lys Ile Pro Leu Gly Gly Ile Pro Ser Pro Ser Thr Glu
    450                 455                 460

Gln Ser Ala Lys Lys Val Arg Lys Lys Ala Glu Asn Ala His Asn Thr
465                 470                 475                 480

Pro Leu Leu Val Leu Tyr Gly Ser Asn Met Gly Thr Ala Glu Gly Thr
                485                 490                 495

Ala Arg Asp Leu Ala Asp Ile Ala Met Ser Lys Gly Phe Ala Pro Gln
            500                 505                 510

Val Ala Thr Leu Asp Ser His Ala Gly Asn Leu Pro Arg Glu Gly Ala
        515                 520                 525

Val Leu Ile Val Thr Ala Ser Tyr Asn Gly His Pro Pro Asp Asn Ala
    530                 535                 540

Lys Gln Phe Val Asp Trp Leu Asp Gln Ala Ser Ala Asp Glu Val Lys
545                 550                 555                 560

Gly Val Arg Tyr Ser Val Phe Gly Cys Gly Asp Lys Asn Trp Ala Thr
                565                 570                 575

Thr Tyr Gln Lys Val Pro Ala Phe Ile Asp Glu Thr Leu Ala Ala Lys
            580                 585                 590

Gly Ala Glu Asn Ile Ala Asp Arg Gly Glu Ala Asp Ala Ser Asp Asp
        595                 600                 605

Phe Glu Gly Thr Tyr Glu Glu Trp Arg Glu His Met Trp Ser Asp Val
    610                 615                 620

Ala Ala Tyr Phe Asn Leu Asp Ile Glu Asn Ser Glu Asp Asn Lys Ser
625                 630                 635                 640

Thr Leu Ser Leu Gln Phe Val Asp Ser Ala Ala Asp Met Pro Leu Ala
                645                 650                 655

Lys Met His Gly Ala Phe Ser Thr Asn Val Val Ala Ser Lys Glu Leu
            660                 665                 670

Gln Gln Pro Gly Ser Ala Arg Ser Thr Arg His Leu Glu Ile Glu Leu
        675                 680                 685

Pro Lys Glu Ala Ser Tyr Gln Glu Gly Asp His Leu Gly Val Ile Pro
    690                 695                 700

Arg Asn Tyr Glu Gly Ile Val Asn Arg Val Thr Ala Arg Phe Gly Leu
705                 710                 715                 720

Asp Ala Ser Gln Gln Ile Arg Leu Glu Ala Glu Glu Lys Leu Ala
                725                 730                 735

His Leu Pro Leu Ala Lys Thr Val Ser Val Glu Glu Leu Leu Gln Tyr
            740                 745                 750

Val Glu Leu Gln Asp Pro Val Thr Arg Thr Gln Leu Arg Ala Met Ala
```

```
                755                 760                 765
Ala Lys Thr Val Cys Pro Pro His Lys Val Glu Leu Glu Ala Leu Leu
770                 775                 780

Glu Lys Gln Ala Tyr Lys Glu Gln Val Leu Ala Lys Arg Leu Thr Met
785                 790                 795                 800

Leu Glu Leu Leu Glu Lys Tyr Pro Ala Cys Glu Met Lys Phe Ser Glu
                805                 810                 815

Phe Ile Ala Leu Leu Pro Ser Ile Arg Pro Arg Tyr Tyr Ser Ile Ser
                820                 825                 830

Ser Ser Pro Arg Val Asp Glu Lys Gln Ala Ser Ile Thr Val Ser Val
                835                 840                 845

Val Ser Gly Glu Ala Trp Ser Gly Tyr Gly Glu Tyr Lys Gly Ile Ala
850                 855                 860

Ser Asn Tyr Leu Ala Glu Leu Gln Glu Gly Asp Thr Ile Thr Cys Phe
865                 870                 875                 880

Ile Ser Thr Pro Gln Ser Glu Phe Thr Leu Pro Lys Asp Pro Glu Thr
                885                 890                 895

Pro Leu Ile Met Val Gly Pro Gly Thr Gly Val Ala Pro Phe Arg Gly
                900                 905                 910

Phe Val Gln Ala Arg Lys Gln Leu Lys Glu Gln Gly Gln Ser Leu Gly
                915                 920                 925

Glu Ala His Leu Tyr Phe Gly Cys Arg Ser Pro His Glu Asp Tyr Leu
930                 935                 940

Tyr Gln Glu Glu Leu Glu Asn Ala Gln Ser Glu Gly Ile Ile Thr Leu
945                 950                 955                 960

His Thr Ala Phe Ser Arg Met Pro Asn Gln Pro Lys Thr Tyr Val Gln
                965                 970                 975

His Val Met Glu Gln Asp Gly Lys Lys Leu Ile Glu Leu Leu Asp Gln
                980                 985                 990

Gly Ala His Phe Tyr Ile Cys Gly Asp Gly Ser Gln Met Ala Pro Ala
                995                 1000                1005

Val Glu Ala Thr Leu Met Lys Ser Tyr Ala Asp Val His Gln Val Ser
1010                1015                1020

Glu Ala Asp Ala Arg Leu Trp Leu Gln Gln Leu Glu Glu Lys Gly Arg
1025                1030                1035                1040

Tyr Ala Lys Asp Val Trp Ala Gly
                1045

<210> SEQ ID NO 17
<211> LENGTH: 20
<212> TYPE: DNA
<213> ORGANISM: Artificial Sequence
<220> FEATURE:
<223> OTHER INFORMATION: primer used for the generation of mutant, SacI-
      F forward

<400> SEQUENCE: 17
atacaaacta cgagctcgat                                              20

<210> SEQ ID NO 18
<211> LENGTH: 27
<212> TYPE: DNA
<213> ORGANISM: Artificial Sequence
<220> FEATURE:
<223> OTHER INFORMATION: primer used for the generation of mutatnt,
      XhoI-R reverse

<400> SEQUENCE: 18
```

```
atcctcgagt tacccagccc acacgtc                                                    27
```